United States Patent
Shiraishi et al.

(10) Patent No.: US 10,741,271 B2
(45) Date of Patent: Aug. 11, 2020

(54) TEST DEVICE AND METHOD OF OPERATING THE SAME

(71) Applicant: FUJIFILM Corporation, Tokyo (JP)

(72) Inventors: Jumpei Shiraishi, Ashigarakami-gun (JP); Yasuko Yahiro, Ashigarakami-gun (JP); Takeshi Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 226 days.

(21) Appl. No.: 15/891,683

(22) Filed: Feb. 8, 2018

(65) Prior Publication Data

US 2018/0166156 A1 Jun. 14, 2018

Related U.S. Application Data

(63) Continuation of application No. PCT/JP2016/070192, filed on Jul. 7, 2016.

(30) Foreign Application Priority Data

Aug. 28, 2015 (JP) ................................ 2015-169277

(51) Int. Cl.
  *G06F 15/173* (2006.01)
  *G16H 10/40* (2018.01)
  (Continued)

(52) U.S. Cl.
  CPC .......... *G16H 10/40* (2018.01); *A61B 5/7445* (2013.01); *G01N 33/48792* (2013.01);
  (Continued)

(58) Field of Classification Search
  CPC ............ A61B 5/14532; A61B 5/14546; A61B 5/0022; A61B 5/1495; A61B 5/14503;
  (Continued)

(56) References Cited

U.S. PATENT DOCUMENTS

| 2003/0105809 A1* | 6/2003 | Yoshii ............... H04L 29/06027 709/203 |
| 2003/0217319 A1* | 11/2003 | Tripathi ............ H03M 13/3738 714/751 |

(Continued)

FOREIGN PATENT DOCUMENTS

| CN | 1760787 A | 4/2006 |
| JP | 2004-289814 A | 10/2004 |

(Continued)

OTHER PUBLICATIONS

Japanese Notification of Reasons for Refusal, dated May 23, 2018, for Japanese Application No. 2015-169277, along with an English machine translation.

(Continued)

*Primary Examiner* — Michael A Keller
*Assistant Examiner* — Thao D Duong
(74) *Attorney, Agent, or Firm* — Birch, Stewart, Kolasch & Birch, LLP

(57) ABSTRACT

The test device is configured of a device main body and a mobile terminal. The mobile terminal functions as an operation terminal of the device main body, and a browsing terminal for measurement data. The mobile terminal is connected to the device main body through wireless communication. The device main body wirelessly transmits the measurement data to the mobile terminal. The mobile terminal notifies the device main body of the reception data size of the measurement data. In the device main body, a determining unit collates the reception data size with the transmission data size of the measurement data and determines whether or not the measurement data is normally transmitted. A notifying unit notifies the mobile terminal of a transmission result showing that non-transmitted data is present.

18 Claims, 26 Drawing Sheets

(51) Int. Cl.
*H04W 28/04* (2009.01)
*H04W 84/12* (2009.01)
*H04L 1/16* (2006.01)
*G01N 35/00* (2006.01)
*A61B 5/00* (2006.01)
*G01N 33/487* (2006.01)
*G01N 33/66* (2006.01)
*G01N 33/70* (2006.01)

(52) U.S. Cl.
CPC ............ *G01N 33/66* (2013.01); *G01N 33/70* (2013.01); *G01N 35/00* (2013.01); *H04L 1/16* (2013.01); *H04W 28/04* (2013.01); *H04W 84/12* (2013.01)

(58) Field of Classification Search
CPC ... A61B 5/1473; A61B 5/1451; A61B 5/7267; G01N 27/3274; G01N 33/49; G01N 27/02; G01N 33/497; G01N 1/30; H05K 999/99; H05K 999/00
See application file for complete search history.

(56) References Cited

U.S. PATENT DOCUMENTS

| | | | |
|---|---|---|---|
| 2004/0024749 A1* | 2/2004 | Kusens | G06F 19/328 |
| 2004/0179232 A1 | 9/2004 | Inukai et al. | |
| 2006/0085650 A1 | 4/2006 | Nakamura | |
| 2006/0116074 A1* | 6/2006 | Kato | H04B 7/155 |
| | | | 455/11.1 |
| 2010/0035334 A1 | 2/2010 | Okuda et al. | |
| 2010/0159835 A1 | 6/2010 | Aoki et al. | |
| 2011/0230743 A1 | 9/2011 | Inciardi et al. | |
| 2012/0197090 A1* | 8/2012 | Chen | A61B 5/0015 |
| | | | 600/301 |
| 2013/0280698 A1* | 10/2013 | Propper | G01N 33/5302 |
| | | | 435/5 |
| 2015/0005608 A1 | 1/2015 | Evans et al. | |

FOREIGN PATENT DOCUMENTS

| | | |
|---|---|---|
| JP | 2005-342121 A | 12/2005 |
| JP | 2009-27659 A | 2/2009 |
| JP | 2009-195679 A | 9/2009 |
| JP | 2009-198491 A | 9/2009 |
| JP | 2010-5276 A | 1/2010 |
| JP | 2011-191204 A | 9/2011 |
| JP | 2013-522650 A | 6/2013 |
| JP | 2015-513413 A | 5/2015 |

OTHER PUBLICATIONS

International Preliminary Report on Patentability and Written Opinion of the International Searching Authority (Forms PCT/IB/326, PCT/IB/373 and PCT/ISA/237) for Application No. PCT/JP2016/070192, dated Mar. 15, 2018, with an English translation.
International Search Report and English translation (Form PCT/ISA/210) for Application No. PCT/JP2016/070192, dated Sep. 6, 2016.
Extended European Search Report for corresponding Application No. 16841282.3, dated Apr. 26, 2018.
Abbott, "precision Xceed Operation manual," retrieved from URL:http://www.for-mylife.jp/precision_xceed.pdf, 2013, pp. 1-58 (66 pages total).
Japanese Decision of Refusal for corresponding Japanese Application No. 2015-169277, dated Dec. 25, 2018, with English translation.
Chinese Office Action and Search Report for Corresponding Chinese Application No. 201680048852.5, dated Mar. 26, 2020, with partial English translation.

* cited by examiner

FIG. 9
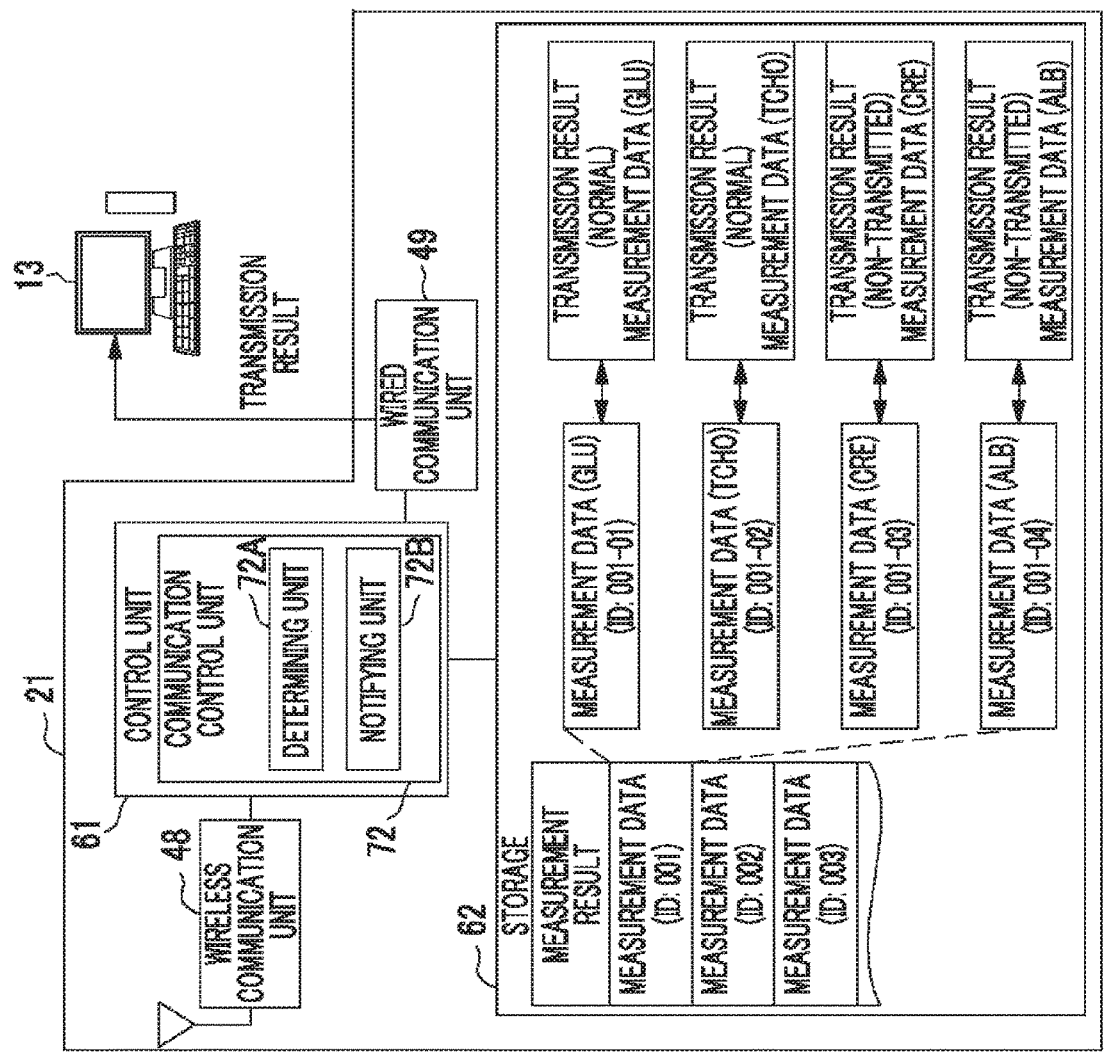
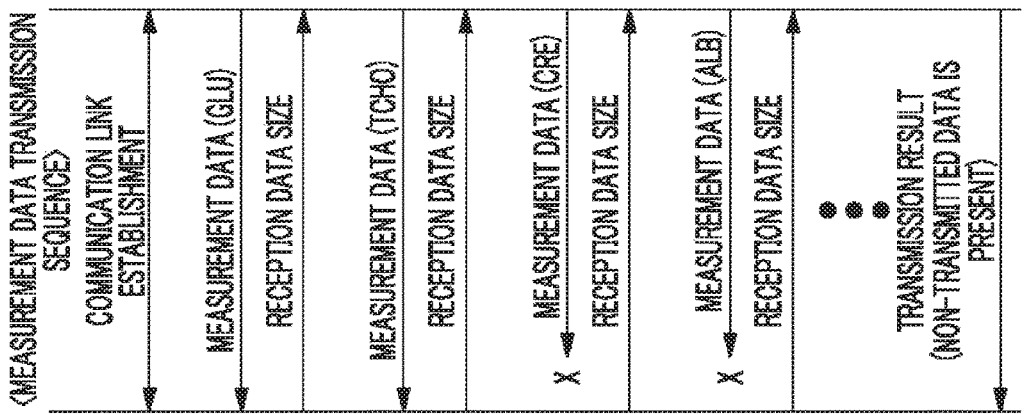
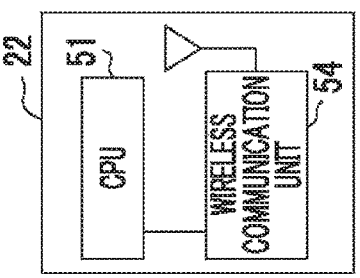

TEST DEVICE AND METHOD OF OPERATING THE SAME

CROSS-REFERENCE TO RELATED APPLICATIONS

This application is a Continuation of PCT International Application No. PCT/JP2016/070192 filed on Jul. 7, 2016, which claims priority under 35 U.S.C. § 119(a) to Japanese Patent Application No. 2015-169277 filed on Aug. 28, 2015. Each of the above application(s) is hereby expressly incorporated by reference, in its entirety, into the present application.

BACKGROUND OF THE INVENTION

1. Field of the Invention

The present invention relates to a test device and a method of operating the same.

2. Description of the Related Art

A clinical test system, which tests blood as a sample collected from a living body and manages a test result in a browsable manner, is known (refer to JP2011-191204A). The clinical test system described in JP2011-191204A includes a blood analysis system 200 that measures blood, a clinical test server 9 that manages test orders and test results, and a client terminal 10 that makes an access to the clinical test server 9 (Paragraph 0029). In a case where the measurement of the blood is completed, the blood analysis system 200 transmits test results to the clinical test server 9 (Paragraph 0051). A user can make an access to the clinical test server 9 through the client terminal 10 to browse the test results (Paragraphs 0043 and 0065).

Additionally, in a case where various errors have occurred in the blood analysis system 200, the clinical test server 9 records the errors. A communication failure (communication abnormality) between a system control device 8, which is a control unit of the blood analysis system 200, and the clinical test server 9 is also included in the errors (Paragraph 0056). The client terminal 10 that has made an access to the clinical test server 9 is notified of the communication failure (Paragraph 0078).

Additionally, the clinical test server 9 is capable of transmitting and receiving the test orders between the clinical test server 9 and a host computer 100 that is an issuer of the test orders (Paragraph 0028). The clinical test server 9 also detects the communication failure between the clinical test server 9 and the host computer 100, and notifies the client terminal 10 of the detected communication failure (Paragraph 0078).

SUMMARY OF THE INVENTION

In the clinical test system of JP2011-191204A, in a case where a communication failure between the blood analysis system (test device) 200 and the clinical test server 9 or a communication failure between the clinical test server 9 and the host computer has occurred, the client terminal 10 that has made an access to the clinical test server 9 is notified of the occurrence of the communication failure.

However, in the clinical test system of JP2011-191204A, notification contents that can be confirmed by a user are limited to the occurrence of the communication failure only. Therefore, there are the following problems.

That is, in a case where a plurality of pieces of measurement data that are test results are present, in a case where a communication failure occurs during the transmission of the plurality of pieces of measurement data, there may be a case where some pieces of measurement data are normally transmitted and only some pieces of measurement data become non-transmitted data. In such a case, since some pieces of measurement data are normally transmitted, even in a case where notification of only the occurrence of the communication failure is provided, there is a concern that the user may not mistakenly notice the presence of the non-transmitted data. Since the measurement data are important data used for diagnosis, the need for preventing overlooking of the non-transmitted data is high.

Additionally, the inventors have been studying a new configuration configured of a device main body having a test unit that executes testing to output measurement data, and a mobile terminal having a display unit that displays the measurement data, as the configuration of the test device. In a case where the measurement data can be browsed in a mobile terminal, a test technician can carry the mobile terminal from a test room to a consultation room or the like, and can make a doctor or a patient browse the measurement data displayed on the mobile terminal. In this way, it is very user-friendly such that comparison with the test results or literature obtained by being measured by other systems can be performed in conferences or the like held in the test room.

In this way, in a case where the new configuration in which the test device is configured of the device main body and the mobile terminal having the display unit is adopted, as compared to the test device of the related art in which the device main body and the display unit are integrated with each other, the occurrence frequency of communication failures becomes high, and the occurrence frequency of the non-transmitted data also becomes high. In order to browse the measurement data with the mobile terminal different from the device main body, the need for wirelessly transmitting the measurement data between the device main body and the mobile terminal arises. This is because the occurrence frequency of communication failures in the case of the wireless transmission becomes higher as compared to wired transmission.

Hence, since the occurrence frequency of the non-transmitted data is high in the test device of the new configuration in which the display unit is configured of the mobile terminal, it is not sufficient to just provide notification of the occurrence of communication failures as in the related art, and a countermeasure for preventing the overlooking of the non-transmitted data is strongly desired.

An object of the present invention is to provide a test device and a method of operating the same that can prevent overlooking non-transmitted data.

In order to achieve the above object, a test device of the present invention includes a device main body and a mobile terminal. The device main body has a test unit and a transmission unit. The test unit tests a sample collected from a living body to output a plurality of pieces of measurement data. The transmission unit wirelessly transmits the measurement data. The mobile terminal has a reception unit and a display unit. The reception unit receives the measurement data wirelessly transmitted from the transmission unit. The display unit displays the received measurement data. The device main body further has a determining unit and a notifying unit. The determining unit determines whether or not the measurement data is normally transmitted to the mobile terminal. In a case where there is non-transmitted data that is not normally transmitted among the plurality of pieces of measurement data, the notifying unit provides notification of a transmission result showing that there is non-transmitted data.

It is preferable that information on whether or not each piece of the measurement data is normally transmitted is included in the transmission result.

It is preferable that the test unit tests a plurality of different samples to output a plurality of pieces of measurement data for each sample, and the measurement data to be transmitted by the transmission unit is the plurality of pieces of measurement data for each sample.

It is preferable that the test unit outputs a plurality of pieces of measurement data relating to a plurality of measurement items in testing of one sample, and the measurement data to be transmitted by the transmission unit is the plurality of pieces of measurement data regarding the plurality of measurement items.

It is preferable that the determining unit receives, from the mobile terminal, notification of a reception result of the measurement data received by the mobile terminal after the measurement data is transmitted, and determines whether or not the measurement data is normally transmitted on the basis of the reception result.

It is preferable that the reception result includes a received data size regarding the measurement data received by the mobile terminal, and the determining unit determines whether or not normal transmission is made by collating a data size of the transmitted measurement data with the received data size notified from the mobile terminal.

It is preferable that the reception result includes received item information showing a measurement item of the measurement data received by the mobile terminal, and the determining unit determines whether or not normal transmission is made by collating a measurement item of the transmitted measurement data with the received item information notified from the mobile terminal.

It is preferable that, in a case where the non-transmitted data is generated due to a communication failure, the notifying unit notifies the mobile terminal of the transmission result in a case where the communication failure is recovered.

It is preferable that the notifying unit notifies a terminal different from the mobile terminal of the transmission result. It is preferable that the mobile terminal functions as an operation terminal of the device main body.

A method of operating a test device of the present invention includes a determination step and a notification step. The test device includes a device main body and a mobile terminal. The device main body has a test unit that tests a sample collected from a living body to output a plurality of pieces of measurement data and a transmission unit that wirelessly transmits the measurement data. The mobile terminal has a reception unit that receives the measurement data wirelessly transmitted from the transmission unit and a display unit that displays the received measurement data. In the determination step, whether or not the measurement data is normally transmitted from the device main body to the mobile terminal is determined. In the notification step, in a case where there is non-transmitted data that is not normally transmitted among the plurality of pieces of measurement data, notification of a transmission result showing that there is the non-transmitted data is provided.

According to the present invention, the test device and the method of operating the same that can prevent overlooking the non-transmitted data can be provided.

BRIEF DESCRIPTION OF THE DRAWINGS

FIG. 9 is an explanatory view of a measurement data transmission sequence.

DESCRIPTION OF THE PREFERRED EMBODIMENTS

First Embodiment

Figure 1:
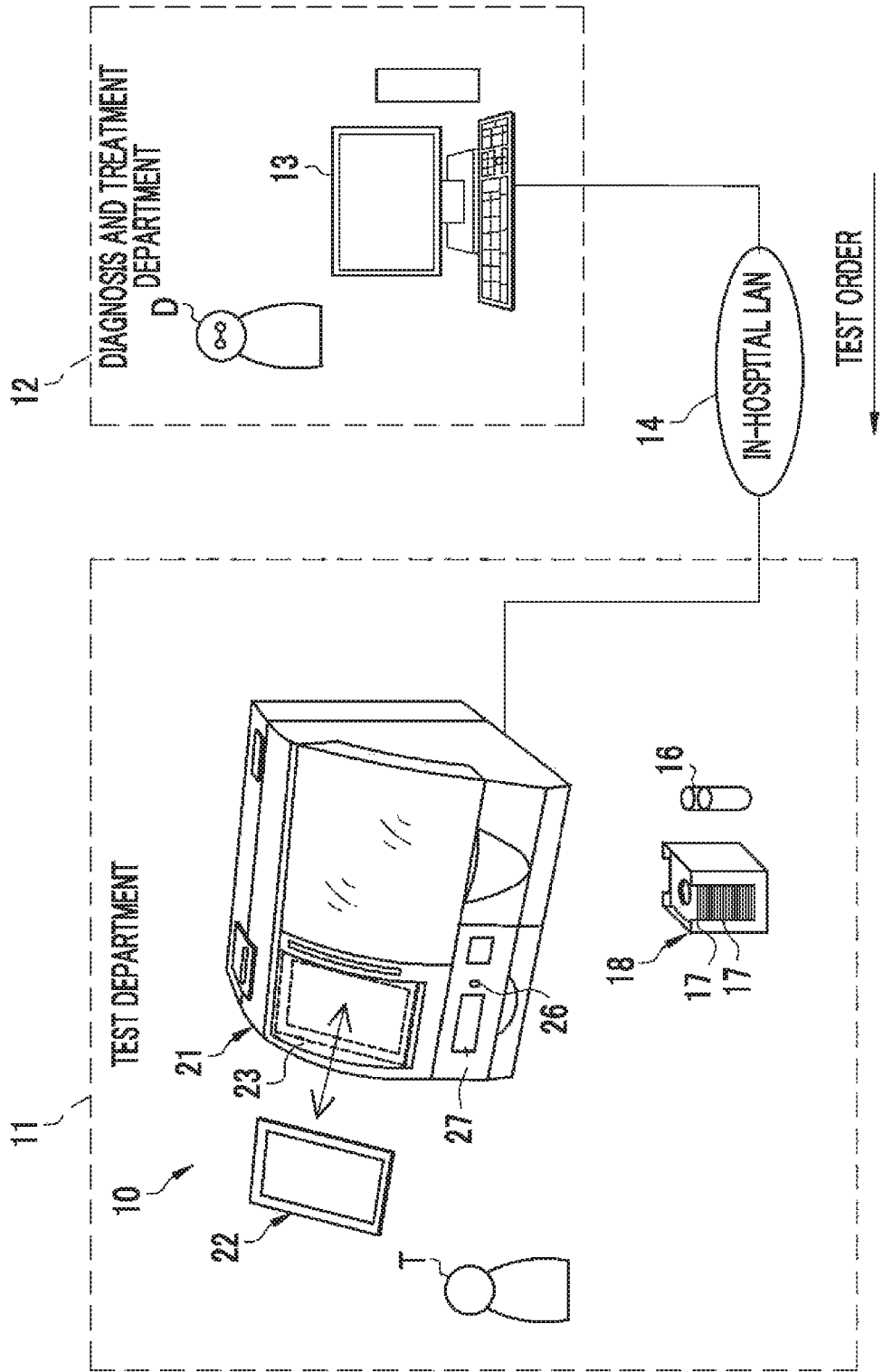
FIG. 1 is an explanatory view of a test device and the inside of a hospital in which the test device is installed.

A test device 10 illustrated in FIG. 1 performs biochemical testing on a sample collected from a living body (including human being and animals), such as blood or urine. The test device 10 is installed, for example, in a test department 11 that is in charge of the biochemical tests within a hospital, and is used by a test technician T. The biochemical test (hereinafter simply referred to as test) is performed on the basis of a test order from a diagnosis and treatment department 12, which is in charge of a patient's medical treatment, such as the internal medicine department or the surgery department.

A diagnosis and treatment department terminal 13 is installed in the diagnosis and treatment department 12. The diagnosis and treatment department terminal 13 is, for example, a client terminal of an electronic chart system, and is capable of making an access to chart database (DB) to browse and update the electronic chart. A doctor D of the diagnosis and treatment department issues a test order by using the diagnosis and treatment department terminal 13. The diagnosis and treatment department terminal 13 and the test device 10 are communicably connected together via, for example, an in-hospital local area network (LAN) 14 that is a communication network within the hospital. The test order issued by the diagnosis and treatment department terminal 13 is transmitted to the test device 10. In a case where the test ends, a test result is transmitted from the test device 10 to the diagnosis and treatment department terminal 13 of the doctor D of a requester.

During the test, samples, such as blood, are collected from the patient. The collected sample is contained in a sample container 16, and is set in the test device 10. The test device 10 measures the contents of chemical components and tangible components contained in the sample by using an analysis slide 17 that is a slide-like dry analysis element. The dry analysis is an analysis method of preparing a reagent, which causes a specific chemical reaction in a dried state, causing a reaction between the reagent in the dried state and the sample, and measuring contained amounts of the chemical components or the like in the sample.

The dry analysis is performed by, for example, a colorimetric method. The colorimetric method is a method of measuring color development density showing a reaction state by subjecting the sample and the reagent to a color development reaction (pigment-producing reaction) to irradiate measuring light.

There are a plurality of kinds of the chemical components or the like in the sample. In the test device 10, measurement is performed on a plurality of measurement items according to the various chemical components or the like. A plurality of types of the analysis slides 17 are prepared in accordance with the plurality of measurement items, and a reagent according to each measurement item is provided in a dried state in each analysis slide 17. The classifications of the biochemical test include, for example, general chemical test, enzyme test, and the like. Among these, the measurement items of the general chemical test include, for example, glucose (GLU), total cholesterol (TCHO), creatinine (CRE), albumin (ALB), and the like. The analysis slides 17 are prepared in accordance with such measurement items.

Additionally, in each analysis slide 17, an item code showing the identification ID (Identification Data) and measurement item of the analysis slide 17 is recorded in the form of a bar cord or the like during manufacturing. The test device 10 reads the item code, thereby identifying which measurement item the analysis slide 17 corresponds to.

Figure 2:
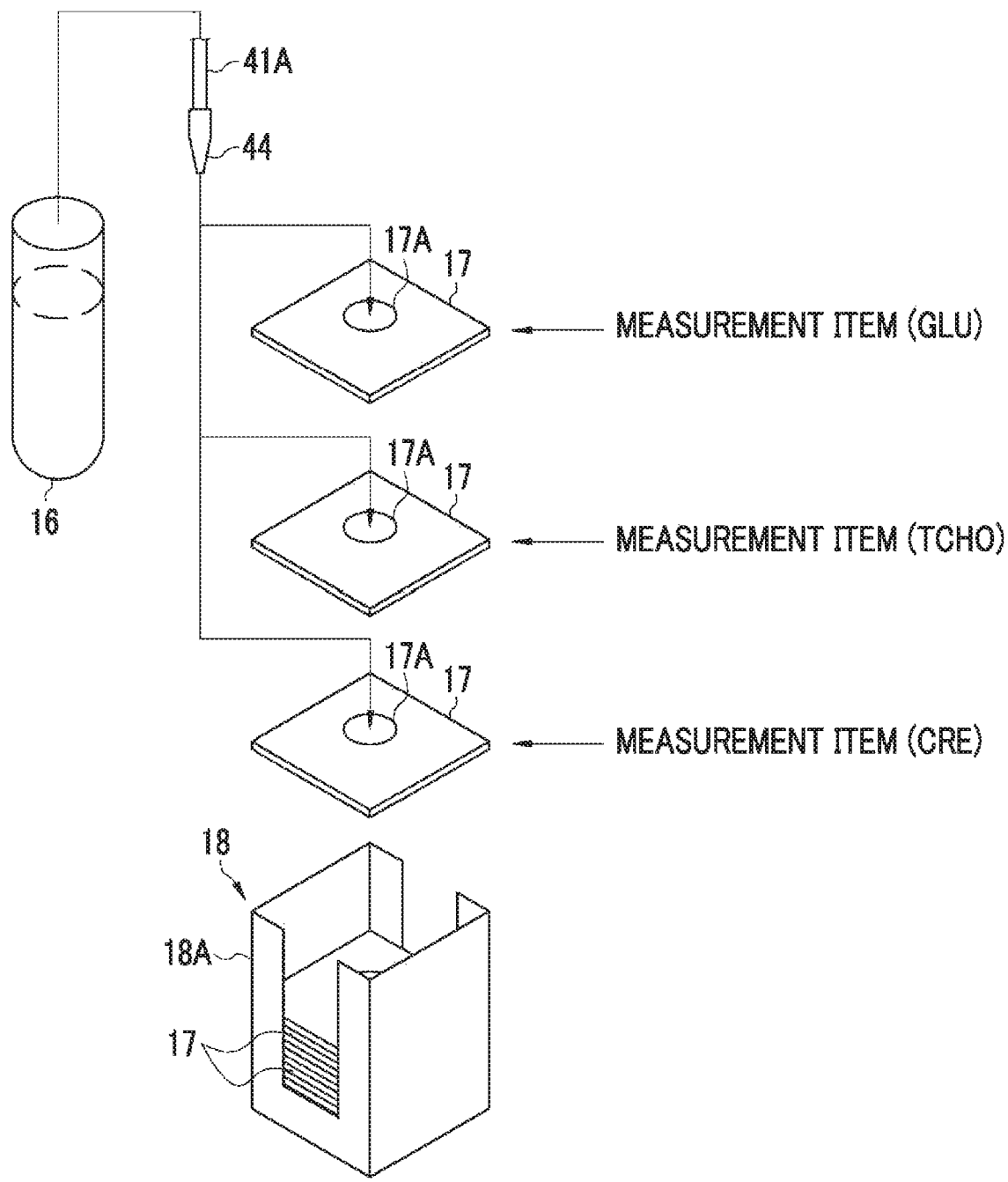
FIG. 2 is an explanatory view of analysis slides and a cartridge.

As illustrated in FIG. 2, a cartridge 18 contains the plurality of analysis slides 17 according to the plurality of measurement items in a storage container 18A. For example, in a case where the general chemical test is performed, the cartridge 18 for the general chemical test in which the plurality of analysis slides 17 according to the plurality of measurement items ("GLU", "TCHO", "CRE", and the like) of the general chemical test are contained is selected. By using the cartridge 18 for the general chemical test, the plurality of measurement items of the general chemical test can be collectively measured.

A spotting hole 17A is formed in each analysis slide 17, and a sample within the sample container 16 is spotted through the spotting hole 17A. The spotting of the sample is performed by a dispenser 41A that is a constituent element of a spotting mechanism 41 (refer to FIG. 3). Reference sign 44 designates a nozzle tip that is replaceably attached to the dispenser 41A.

In addition, a measurement method for the dry analysis includes an electrode method other than the colorimetric method. The electrode method is a method of measuring an electrolyte (ions), such as sodium or potassium in the sample, depending on a potential difference from a reference solution. Specifically, the electrode method is a method of measuring the potential between the reference solution and the sample with an electrode to measure the ionic activity of the sample after the sample and the reference solution whose ionic activity is known is reacted with reagents, respectively. Measurement of the electrode method is also possible for the test device 10, and in a case where the measurement is performed by the electrode method, an electrolyte type analysis slide 17 is used.

With respect to one test order, the sample container 16 for a sample to be tested and the cartridge 18 that contains the plurality of analysis slides 17 are prepared, and one set of the sample container 16 and the cartridge 18 is set in the test device 10.

Figure 3:
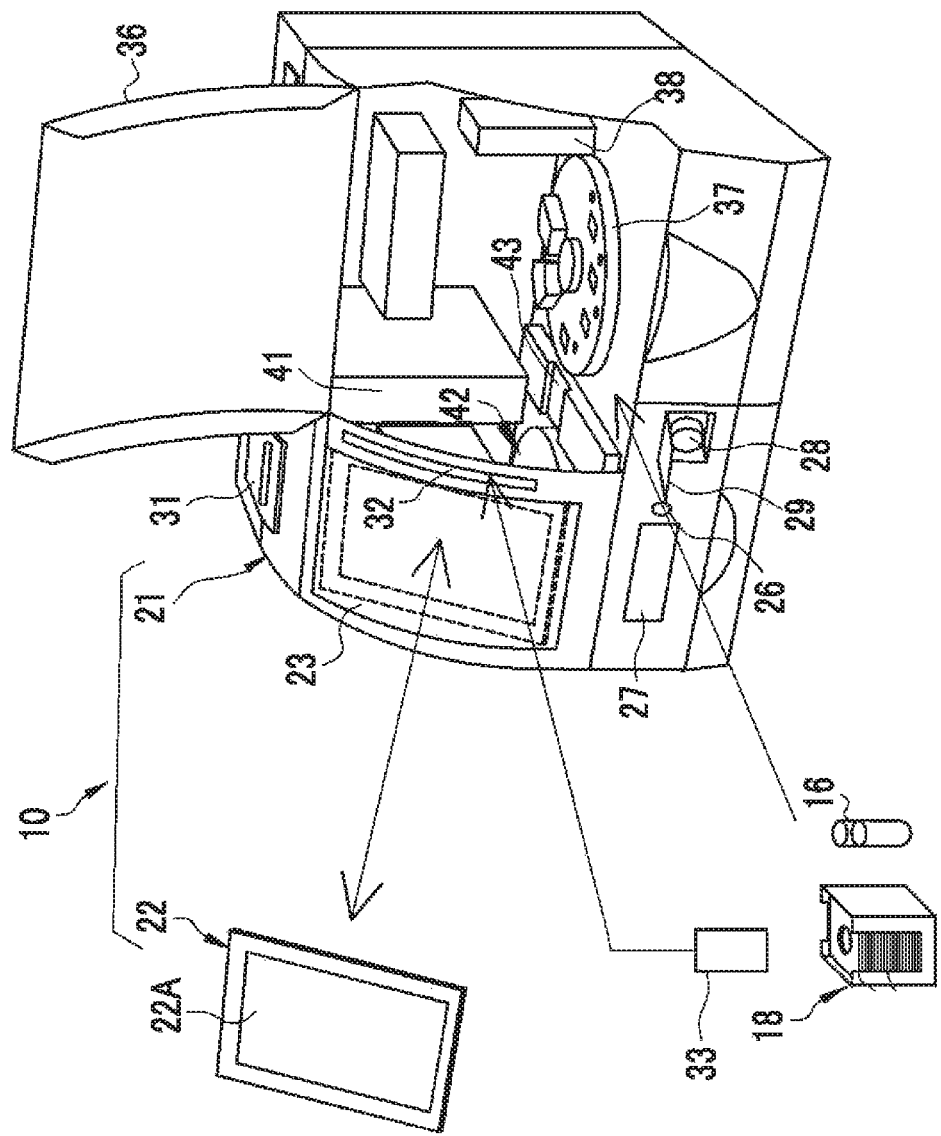
FIG. 3 is an explanatory view of the test device.

As illustrated in FIGS. 1 and 3, the test device 10 includes a device main body 21 and a mobile terminal 22. The mobile terminal 22 functions as an operation terminal for operating the device main body 21, and a browsing terminal for browsing a test order and measurement results. The mobile terminal 22 is configured of, for example, a tablet type computer that has a touch panel display (hereinafter simply referred to as a touch panel) 22A, which also serves as a display and an input device, and is capable of wireless communication. The communication between the mobile terminal 22 and the device main body 21 is wirelessly performed.

The mobile terminal 22 is attachable to and detachable from the device main body 21, and is also capable of being used in the state of being mounted on the device main body 21. The device main body 21 is provided with a mounting unit 23 on which the mobile terminal 22 is mounted. The mobile terminal 22 can be used like an operation panel provided on the device main body 21 in a state where the mobile terminal 22 is mounted on the mounting unit 23.

On a front surface of the device main body 21, a power source lamp 26 and a liquid crystal display (LCD) 27 are provided at a lower part of the mounting unit 23. The power source lamp 26 is an indicator that notifies the input state (ON/OFF) of a power source, and the LCD 27 is a display unit that notifies an error message and the status of the device main body 21.

ON/OFF of the power source of the device main body 21 is performed by the operation from the mobile terminal 22. By providing the power source lamp 26, the input state of the power source can be confirmed even in a state where the mobile terminal 22 is detached from the device main body 21. Additionally, the error message and the status of the device main body 21 are also notified on the mobile terminal 22. However, by providing the LCD 27, a main error message and status can be confirmed by the device main body 21 even in the state where the mobile terminal 22 is detached.

A start switch 28 for inputting a measurement start instruction is provided beside the power source lamp 26. The input of the measurement start instruction is performed mainly through an operation screen of the mobile terminal 22 as will be described below. However, in case of emergency, the measurement start instruction may be input even from the device main body 21. For that reason, the device main body 21 is provided with the start switch 28. However, in a case where a double operation is performed by the mobile terminal 22 and the start switch 28, there is also a concern that a problem may occur. For that reason, a cover 29 that covers the start switch 28 when not in use is provided on the device main body 21 such that the start switch 28 may not be carelessly operated.

A paper ejection port 31 of a printer 66 (refer to FIG. 7) is provided on an upper surface of the device main body 21. The test device 10 is adapted to be capable of selecting print output as an output form of measurement results. The paper ejection port 31 ejects a sheet on which the printer 66 has printed the measurement results.

Additionally, a slit 32 of a card reader 63 (refer to FIG. 7) is provided beside the mounting unit 23. The slit 32 is for allowing a card 33 (hereinafter referred to as a calibration card) for calibration, which is provided while being attached to the analysis slide 17, to pass therethrough. Although the analysis slide 17 is provided with the reagent in the dried state, there is an individual difference in the color development density of the reagents between the manufacturing lots of the analysis slides 17. Since the individual difference of the color development density becomes an error in the measurement data, the calibration according to each analysis slide 17 is required before measurement.

Calibration information acquired during the manufacturing of the analysis slide 17 is recorded as, for example, magnetic information on the calibration card 33. In a case where the calibration card 33 is allowed to pass through the slit 32, the card reader 63 reads the calibration information from the calibration card 33. The device main body 21 executes calibration on the basis of this calibration information. By performing the calibration using the calibration card 33, the individual difference between the analysis slides 17 can be simply corrected.

As illustrated at an inner part of a front cover 36, a sample plate 37, a centrifugal separation mechanism 38, a conveying mechanism 69 (refer to FIG. 7), the spotting mechanism 41, and a test unit 42 are provided inside the device main body 21. The sample plate 37 is a loading unit that loads the sample container 16 serving as a sample and the cartridge 18.

Figure 4:
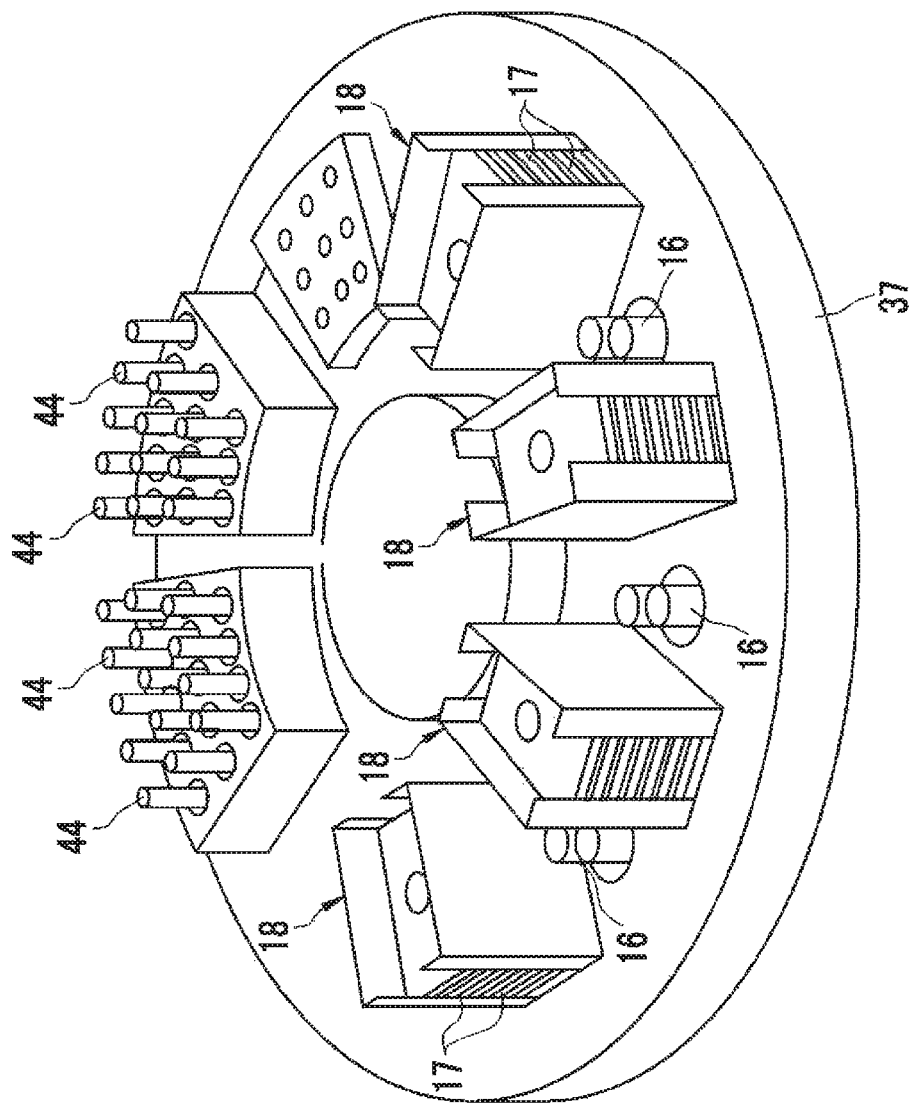
FIG. 4 is an explanatory view of a sample plate.

As illustrated in FIG. 4, the sample plate 37 can be loaded with, for example, a total of four sample sets, with one sample container 16 and one cartridge 18 as one sample set. The test device 10 can continuously execute the testing of the four sample sets. Sample ports that are loading points loaded with the respective sample sets are numbered from 1 to 4, and for example, the test is executed in order according to the port number.

Additionally, the sample plate 37 is loaded with consumables to be used for the test other than the sample sets. The consumables include the nozzle tip 44 of the dispenser 41A (refer to FIG. 2) that is a constituent element of the spotting mechanism 41, a mixing cup (not illustrated) for diluting a sample, a container (not illustrated) that contains a diluting solution that dilutes the sample, a container (not illustrated) that contains the reference solution, and the like. The sample plate 37 is rotatably provided by the driving of a motor, and rotates to a required position.

The centrifugal separation mechanism 38 is a mechanism for separating the blood, which is a sample, into blood cell components including red blood cells and white blood cells and plasma (or blood serum) to extract plasma (or blood serum). The centrifugal separation mechanism 38 is separated into the blood cell component and the plasma (or blood serum) using a difference in specific gravity by rotating the container containing the blood to applying a centrifugal force on the blood within the container. The plasma (or blood serum) is used for quantitative analysis of chemical components in the blood. In addition, the method of separating the components (the plasma, the blood cell component, and the like) of the blood may be other than the centrifugal separation method according to the centrifugal separation mechanism 38. The methods other than the centrifugal separation method include, for example, a filtration method of making blood flow through a filter to extract a target component. In this case, a filtering mechanism is provided instead of the centrifugal separation mechanism 38.

The spotting mechanism 41 is a mechanism that spots a sample onto an analysis slide 17 disposed on the spotting stage 43. The analysis slide 17 is taken out from a cartridge 18 loaded into the sample plate 37, and is conveyed to the spotting stage 43. As described above, the spotting mechanism 41 dispenses the sample within the sample container 16 to the plurality of analysis slides 17 within the cartridge 18 with the dispenser 41A.

The conveying mechanism 69 (refer to FIG. 7) conveys the analysis slide 17 from the cartridge 18 loaded into the sample plate 37 to the spotting stage 43, and further conveys the analysis slide 17, on which the sample is spotted, to the test unit 42. The conveyance of the analysis slide 17 is performed as follows.

First, a cartridge 18 is moved to a position facing the spotting stage 43 by the rotation of the sample plate 37. In the cartridge 18, a lower part of the storage container 18A is provided with a delivery port for analysis slide 17, and the conveying mechanism 69 delivers one analysis slide 17 at a time from the delivery port to the spotting stage 43. Then, the sample is spotted onto the analysis slide 17 on the spotting stage 43 by the spotting mechanism 41. Then, the conveying mechanism 69 conveys the analysis slide 17, onto which the spotting ends, to the test unit 42.

Figure 5:
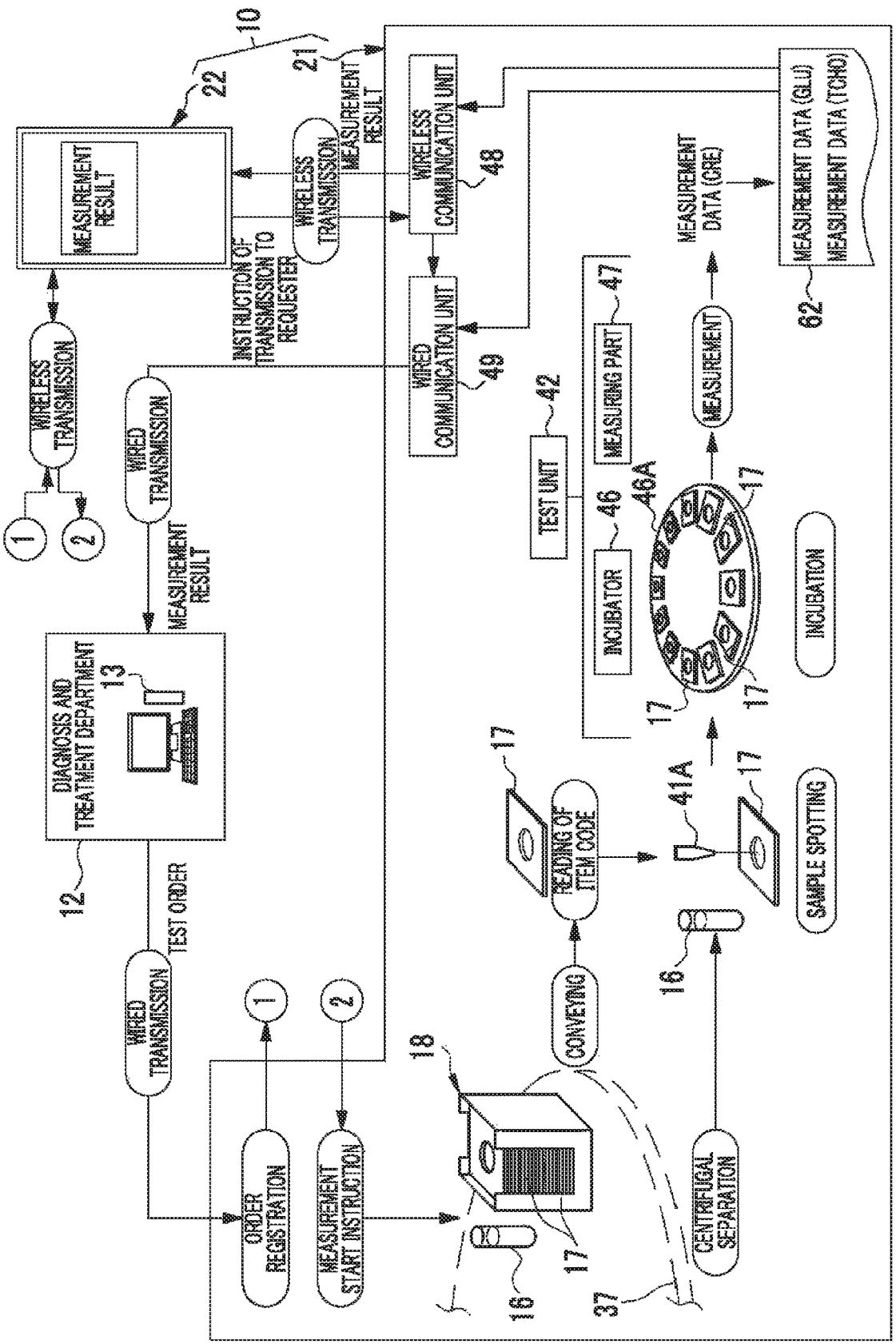
FIG. 5 is an explanatory view of a workflow for testing.

FIG. 5 illustrates a workflow from the issue of a test order by the diagnosis and treatment department terminal 13 through the execution of test based on the test order in the test device 10 to the transmission of the test result to the diagnosis and treatment department terminal 13 of a requester for the test order. As described above, wired transmission of the test order from the diagnosis and treatment department terminal 13 is transmitted to the device main body 21 by wire via of an in-hospital LAN 14. The device main body 21 registers the received test order.

The mobile terminal 22 wirelessly makes an access to the device main body 21, and acquires the registered test order. Accordingly, the test technician T can browse the test order. The test technician T confirms the contents of the test order, and prepares a sample container 16 containing the collected sample and a cartridge 18 including an analysis slide 17 according to the type of test specified by the test order. A sample set having the prepared sample container 16 and cartridge 18 as one set is loaded into the sample plate 37 of the device main body 21. After the sample set is loaded, a calibration card 33 attached to the analysis slide 17 is allowed to pass through the slit 32 and calibration information is input.

In a case where there are a plurality of test orders, the sample plate 37 is loaded with sample sets according to the contents of the test orders in the same procedure. Additionally, input of calibration information according to the loaded sample sets is performed.

After the loading of the sample set to be tested is completed, the front cover 36 is closed and a measurement start instruction is input. The measurement start instruction is input to the device main body 21 through wireless transmission from the mobile terminal 22.

In a case where the measurement start instruction is input, the device main body 21 starts preprocessing. As the preprocessing, centrifugation, item code reading, and sample spotting are performed. In the centrifugation, plasma (or blood serum) is extracted from the blood, which is the sample, by the centrifugal separation mechanism 38.

The analysis slide 17 is pulled out by the conveying mechanism 69 from the cartridge 18, and is conveyed to the spotting stage 43. An item codes showing a measurement item and an identification ID are read from the conveyed analysis slide 17 by a bar code reader 64. Thereafter, the sample is spotted onto the analysis slide 17 on the spotting stage 43 by the dispenser 41A of the spotting mechanism 41. After the sample spotting, the analysis slide 17 is conveyed from the spotting stage 43 to the test unit 42 by the conveying mechanism 69.

The test unit 42 has an incubator 46 and a measuring part 47. The incubator 46 has a plate 46A on which a plurality of analysis slides 17 are placed, and heating means (not illustrated), and in the colorimetric method, the incubator 46 keeps (incubates) an analysis slide 17, onto which a sample is spotted, at constant temperature to cause a color development reaction (pigment-producing reaction). The analysis slide 17 after the sample spotting is incubated in the state of being placed on the plate 46A of the incubator 46.

The test device 10 records a correspondence relationship between the measurement item according to the read item code, and the positional information on the analysis slide 17 of the plate 46A of the incubator 46. This correspondence relationship shows which measurement item the analysis slide 17 disposed at any position on the plate 46A corresponds to. By virtue of this correspondence relationship, it is possible to record the measurement data obtained from each analysis slide 17 in correspondence with the measurement item.

After the completion of the incubation, measurement is performed by the measuring part 47. The measuring part 47 has a measuring unit for the colorimetric method, and a measuring unit for the electrode method. The measuring unit for the colorimetric method has a light source that radiates measuring light with a predetermined wavelength to the analysis slide 17 that has caused the color development reaction, and a sensor that receives the reflected light from the analysis slide 17 to measure a color development density according to the measurement item. Additionally, in the measuring unit for the electrode method, the measuring part 47 has a probe for measure the ionic activity.

Each analysis slide 17 on the plate 46A moves to a position facing a measuring part sequentially by the rotation of the plate 46A, and measurement is performed at that position. The measuring part 47 outputs measurement data for each analysis slide 17, and stores the output measurement data in a data storage device (hereinafter simply referred to as a storage) 62. For example, in a case where a first analysis slide 17 is measured, the measurement data thereof is stored in the storage 62.

In this case, the measuring part 47 determines which measurement item the read measurement data correspond to on the basis of the correspondence relationship between the item code and the positional information, which is recorded in advance, and records the item code (measurement item) in correspondence with the measurement data. An example of FIG. 5 shows an aspect in which measurement data (GLU), measurement data (TCHO), and measurement data (CRE) of respective measurement items of glucose (GLU), total cholesterol (TCHO), and creatinine (CRE), are sequentially output from the measuring part 47.

Figure 6:
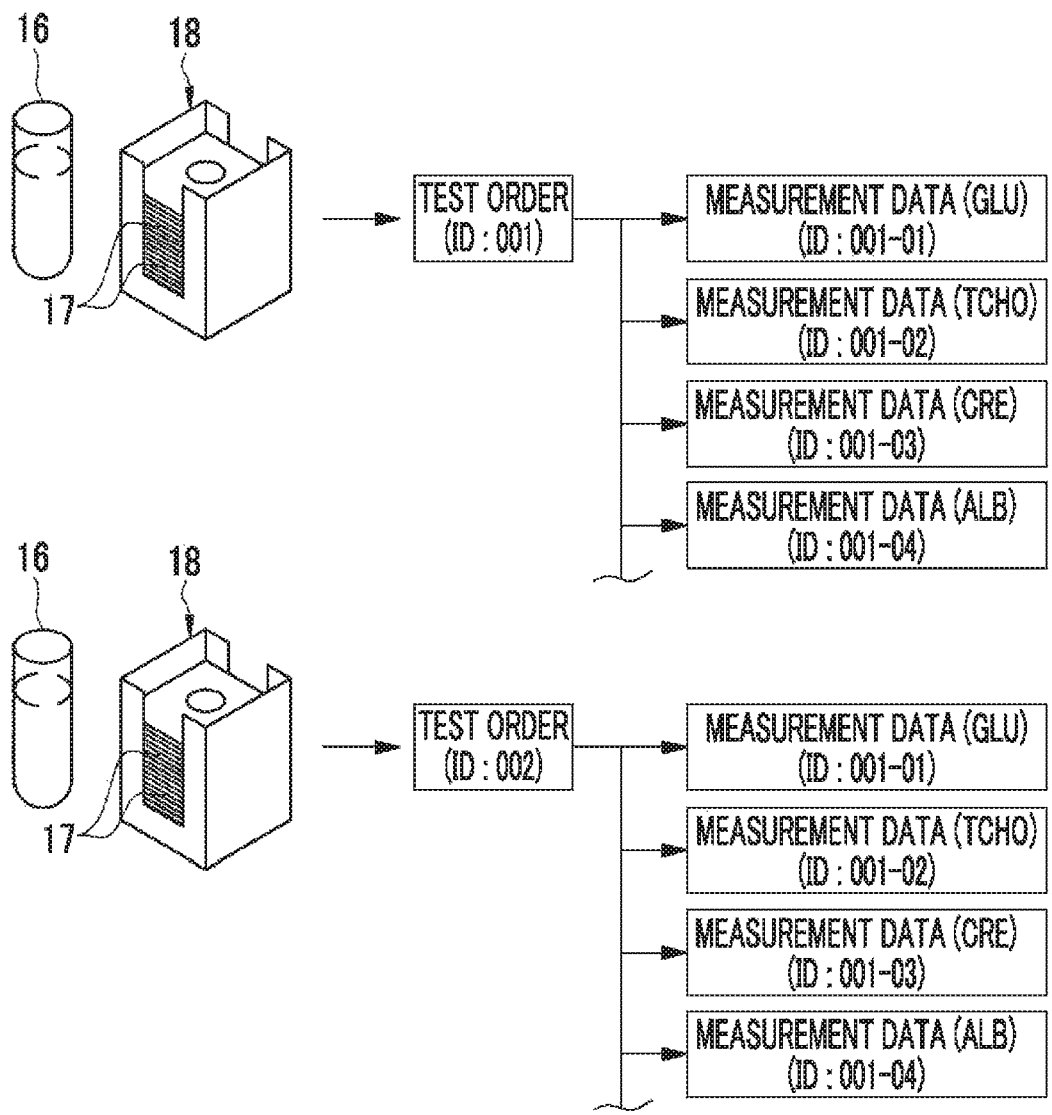
FIG. 6 is an explanatory view of measurement data.

As illustrated in FIG. 6, a plurality of kinds of measurement data corresponding to a plurality of measurement items are output to the test order of one sample. Respective kinds of measurement data are stored in correspondence with IDs ("001" and "002") of the test orders.

After all measurements corresponding to one test order are completed, the device main body 21 transmits a plurality of kinds of measurement data corresponding to the one test order to the mobile terminal 22 as measurement results. The device main body 21 includes a wireless communication unit 48 for communicating with the mobile terminal 22, and a wired communication unit 49 for performing wired communication, such as connection with the in-hospital LAN 14. The measurement results are transmitted to the mobile terminal 22 via the wireless communication unit 48. Accordingly, the measurement results can be browsed by the mobile terminal 22. Here, the wireless communication unit 48 functions as a transmission unit that wirelessly transmits the measurement data.

The test technician T transmits the measurement results to the doctor D of the diagnosis and treatment department 12 of the requester as test results for the test order in a case where the measurement results are confirmed in the mobile terminal 22. The transmission to the requester is performed, for example, by inputting a transmission instruction toward the requester from the mobile terminal 22 to the device main body 21. The device main body 21 transmits the measurement results by wire via the wired communication unit 49 at the diagnosis and treatment department terminal 13 of the requester in a case where the transmission instruction is input. Accordingly, the doctor D of the requester can browse the measurement results.

In addition, the measurement results to the requester may be automatically transmitted from the mobile terminal 22 or the device main body 21 without performing the transmission instruction toward the requester from the mobile terminal 22 to the device main body 21. As automatically transmitted timing, transmission is performed, for example, at a timing (the input operation or the like of a confirmation button) at which the test technician confirms the measurement results in the mobile terminal 22 and confirms that test has normally ended.

Figure 7:
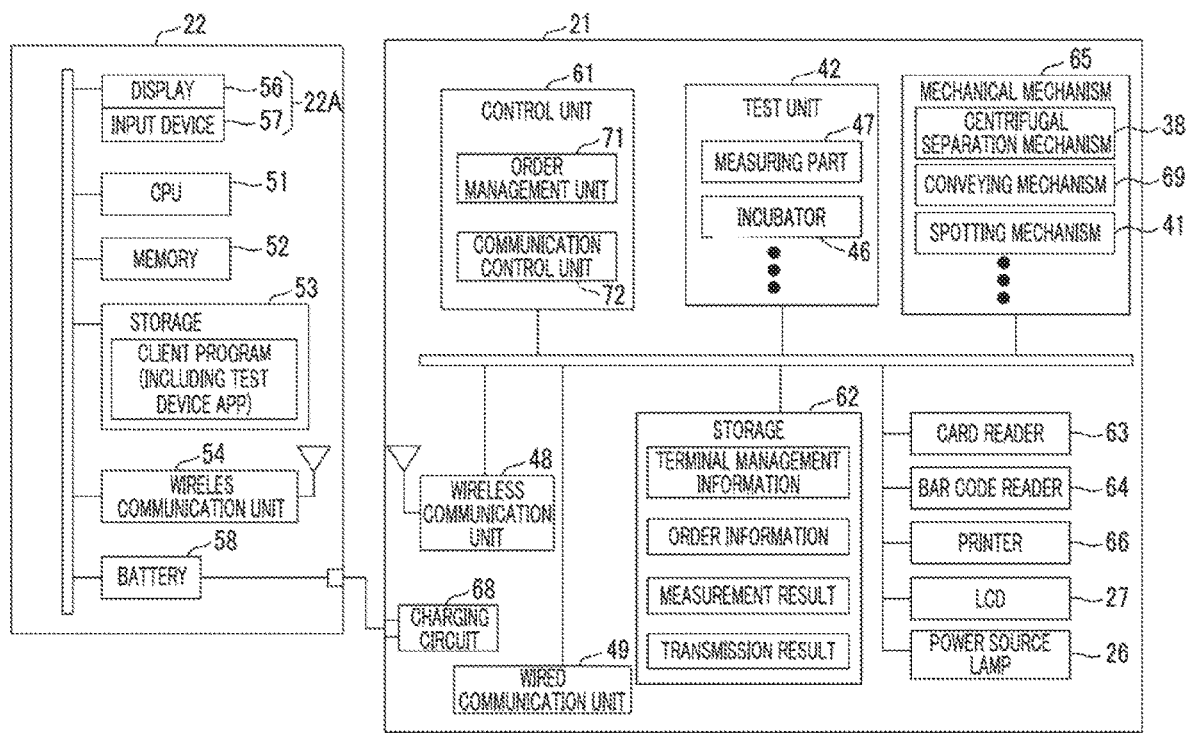
FIG. 7 is a functional block diagram of the test device.

As illustrated in FIG. 7, the mobile terminal 22 is one in which a test device application program (test device application) that realizes an operation function and a measurement result browsing function of the device main body 21 is installed based on a general-purpose tablet type computer. Various client programs are installed in the mobile terminal 22, and the test device application program is one of the client programs.

A schematic configuration of the mobile terminal 22 is the same as that of a general computer, and includes a central processing unit (CPU) 51, a memory 52, a storage 53, a wireless communication unit 54, and a touch panel 22A. These are connected to one another via data buses.

The touch panel 22A functions as a display 56, and an input device 57 that performs input operation through an operation screen displayed on the display 56. The touch panel 22A is a display unit that displays the measurement data received from the device main body 21. Additionally, the mobile terminal 22 is provided with a chargeable battery 58.

The storage 53 is, for example, a hard disk drive (HDD) and a solid-state drive (SSD), and stores a control program and various client programs.

The memory 52 is a work memory for the CPU 51 to execute processing, and is configured of a random access memory (RAM). The CPU 51 integrally controls respective parts of the computer by loading the control program stored in the storage 53 into the memory 52 to execute processing according to the program. The wireless communication unit 54 is, for example, a wireless communication interface based on wireless LAN standards, such as IEEE802.11. The wireless communication unit 54 functions as a reception unit that receives the measurement data wirelessly transmitted from the wireless communication unit 48 of the device main body 21.

The device main body 21 includes a control unit 61, the test unit 42, a mechanical mechanism 65, the storage 62, the card reader 63, the bar code reader 64, the printer 66, the LCD 27, the power source lamp 26, the wireless communication unit 48, the wired communication unit 49, and a charging circuit 68.

The card reader 63 includes a magnetic information reading sensor for reading the magnetic information recorded on the calibration card 33. The bar code reader 64 includes an image sensor for reading the bar code recorded on the analysis slide 17.

In addition, as the calibration card 33, a card on which a one-dimensional bar code or a two-dimensions bar code, such as a quick response (QR) code (registered trademark), is recorded may be used instead of a card on which the magnetic information is recorded. In this case, the card reader 63 is a bar code reader including the image sensor for reading the bar cord. Additionally, in a case where the card reader 63 is the bar code reader, a single image sensor may be made to serve as both the card reader 63 and the bar code reader 64.

As described above, the test unit 42 has the measuring part 47 and the incubator 46, and performs test including measurement of the chemical components contained in the sample. The mechanical mechanism 65 is configured of the centrifugal separation mechanism 38, the conveying mechanism 69, the spotting mechanism 41, and the like.

The wireless communication unit 48 is a wireless communication interface based on wireless LAN standards, such as IEEE802.11, similar to the wireless communication unit 48 of the mobile terminal 22. The wired communication unit 49 is a wired communication interface based on wired LAN standards, such as IEEE802.3. The wireless communication unit 48 and the wired communication unit 49 perform communication in accordance with a typical transmission control protocol/Internet protocol (TCP/IP) as a protocol of LAN.

The charging circuit 68 is a circuit that charges the battery 58 of the mobile terminal 22. A connector of the charging circuit 68 is provided at the mounting unit 23, and in a case where the mobile terminal 22 is mounted on the mounting unit 23, the connector is connected to the mobile terminal 22 and charge is started.

As the standards of the connector of the charging circuit 68, for example, a universal serial bus (USB) is used. Additionally, the connector of the charging circuit 68 may be used as a mounting detection sensor that detects whether or not the mobile terminal 22 is mounted.

In addition, in the present example, the charging of the mobile terminal 22 is performed by the charging circuit 68 built in the device main body 21. However, it is natural that a method of charging the mobile terminal 22 is not limited to this, and the charging of the mobile terminal 22 may be performed by a separate charger (not illustrated).

Depending on the operating status of the device main body 21, it may be disadvantageous in a case where the mobile terminal 22 is detached. For example, in a case where the calibration of the device main body 21 is executed, there is also a case where the device main body 21 performs the calibration while taking a synchronization through communication with the mobile terminal 22. In such a case, the processing cannot be continued in a case where the mobile terminal 22 is detached from the device main body 21. Thus, in a specific operating status, it is preferable to detect the detachment of the mobile terminal 22 from the device main body 21 with the mounting detection sensor, to issue a warning that the mobile terminal 22 should not be detached and the mobile terminal 22 should be mounted on the device main body 21. The warning is displayed, for example, on the LCD 27.

The control unit 61 integrally controls the respective parts of the device main body 21. The control unit 61 is configured of, for example, a CPU and memories as hardware, and is realized in a case where the CPU executes the control program. The control unit 61 has an order management unit 71 and a communication control unit 72. The order management unit 71 performs management of the test order, such as the registration of the received test order and the measurement results corresponding to the test order.

The communication control unit 72 controls wireless communication with the mobile terminal 22. Specifically, the certification processing of the mobile terminal 22 and the monitoring as to whether or not the measurement data is normally transmitted to the mobile terminal 22 are performed. Then, the transmission results of the measurement data are recorded and the recorded transmission results are notified of the mobile terminal 22 or the diagnosis and treatment department terminal 13 of the requester.

The storage 62 is configured of, for example, a hard disk drive (HDD) and a solid-state drive (SSD), similar to the storage 53. Terminal management information, order information, the measurement results, and the transmission results are stored in the storage 62. The terminal management information is information for managing the mobile terminal 22 capable of making an access to the device main body 21. It is also possible to make an access to one device main body 21 from a plurality of the mobile terminals 22. In a case where the device main body 21 can be accessed from the plurality of mobile terminals 22, for example, even in a case where one mobile terminal 22 is carried out of a test room, this is convenient because the operation of the device main body 21 is possible using a separate mobile terminal 22. The mobile terminal 22 capable of making an access to the device main body 21 is managed using the terminal management information.

Figure 8:
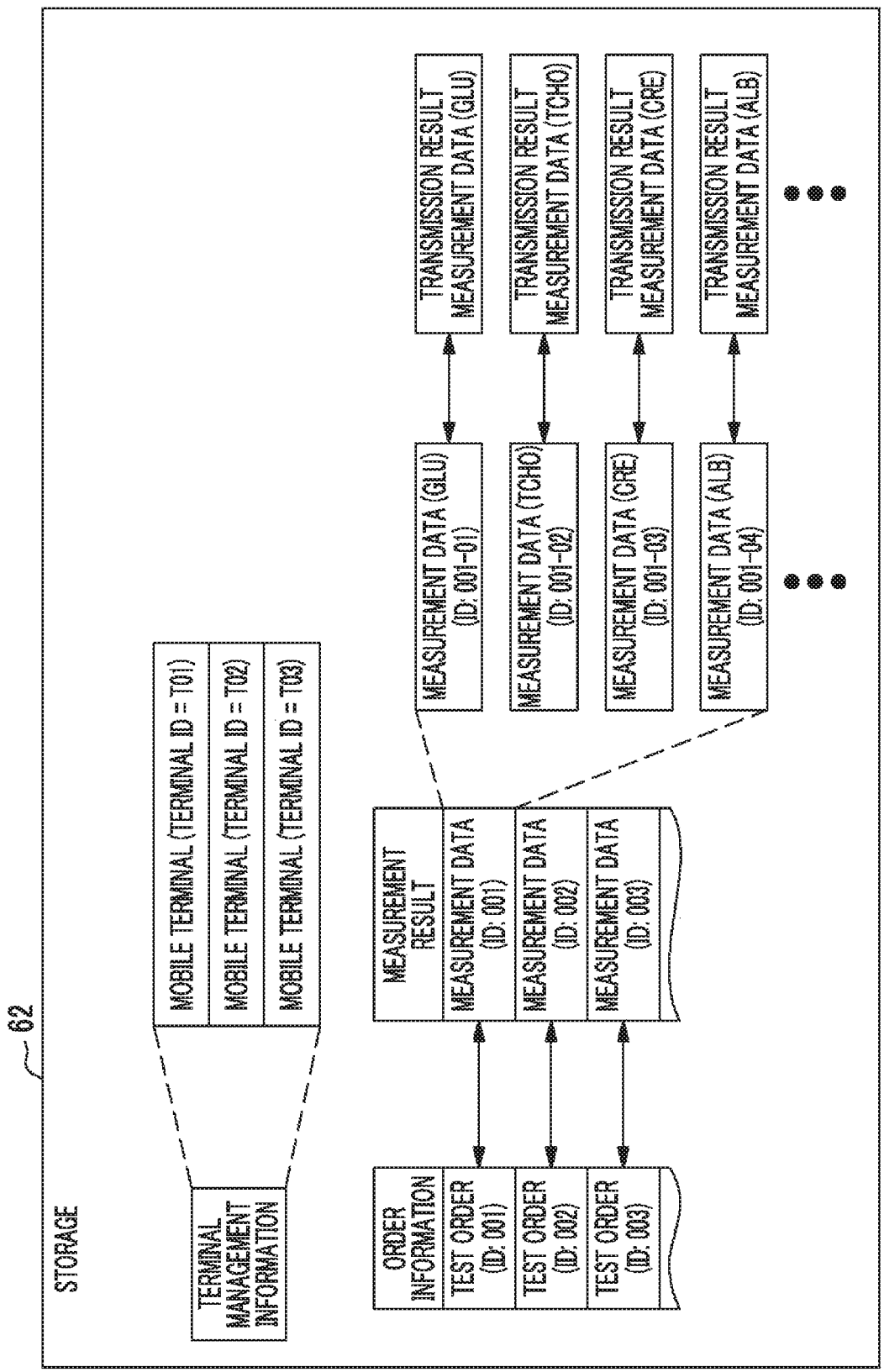
FIG. 8 is an explanatory view of the data to be stored in a storage.

As illustrated in FIG. 8, terminal IDs ("T01", "T02", and "T03") of the mobile terminals 22 that permit access to the device main body 21 are recorded in the terminal management information. As the terminal IDs, specifically, media access control (MAC) addresses are used. As is widely known, the MAC addresses are physical addresses that are uniquely allocated to hardware, such as communication modules, and a MAC address can be used as a terminal ID for identifying the mobile terminal 22. The MAC address is included in header information to be added to all the data with which the mobile terminal 22 performs communication.

The communication control unit 72 determines whether or not the mobile terminal 22 has access authority with reference to the terminal management information, in a case where there is an access from the mobile terminal 22 to the device main body 21 through communication. Then, access is permitted to the mobile terminal 22 having the access authority, and access is rejected to the mobile terminal 22 that does not have the access authority.

In addition, a device ID of the device main body 21 is registered for the mobile terminal 22. The mobile terminal 22 determines whether or not the access from the device main body 21 is permitted with reference to the registered device ID in a case where there is an access from the device main body 21 to the mobile terminal 22. As the device ID, for example, a serial number of the device main body 21 is used. Of course, instead of the serial number, a MAC address allocated to each communication module may be used similar to the terminal ID.

In FIG. 8, the order information is information on a plurality of registered test orders ("ID: 001", "ID: 002", and "ID: 003"). The measurement results are measurement data ("ID: 001", "ID: 002", and "ID: 003") corresponding to the test orders, respectively. In a case where a plurality of measurement items are included in the contents of one test order, measurement data of the plurality of measurement items are included in the measurement results of the one test order. In the example of FIG. 8, measurement data ("ID: 001-01", "ID: 001-02", "ID: 001-03", "ID: 001-04", ...) of a plurality of measurement items of "GLU", "TCHO", "CRE", "ALB", ... are included in the measurement data ("ID: 001") of one test order of "ID: 001".

The transmission results are information showing whether or not the respective items of measurement data are normally transmitted from the device main body 21 to the mobile terminal 22 or whether or not there is any non-transmitted data that is not normally transmitted. Here, the expression "normally transmitted" means that measurement data to be transmitted is transmitted to a transmission destination without missing. The transmission results are recorded, for example, in the respective items of measurement data ("GLU", "TCHO", "CRE", "ALB").

The communication control unit 72 wirelessly transmits information, such as the test orders, the measurement data, and the transmission results, which are stored in the storage 62, to the mobile terminal 22 through the wireless communication unit 48. As will be described below, the mobile terminal 22 displays the information acquired from the device main body 21 as a worklist screen 84 (refer to FIG. 10), a measurement result display screen 91 (refer to FIG. 12), and a transmission result display screen 94 (refer to FIG. 13).

In addition, in a case where the device main body 21 receives a new test order through of the in-hospital LAN 14 to register the new test order in the storage 62, the communication control unit 72 notifies the mobile terminal 22 that the new test order is registered. Accordingly, the test technician T can be informed that there is the new test order.

The measurement data among the data acquired from the device main body 21 is important data to be used for diagnosis. For that reason, strict communication error checking is performed on to wireless transmission of the measurement data by the communication control unit 72 as compared to communication of other data.

In the case of the wireless communication, a communication failure occurs due to an obstacle that cuts off electromagnetic waves, the influence of the electromagnetic waves emitted from other electronic apparatuses, interference with electric waves emitted from other telecommunication apparatuses, or the like. Additionally, even in a case where the mobile terminal 22 moves during communication and the mobile terminal 22 deviates from a communicable range that is a range where electric waves reach between the mobile terminal 22 and the device main body 21, a communication failure occurs.

As is widely known, even in the wireless LAN standards, communication error checking using header information of a data packet that is a transmission unit of data is performed in the protocol of TCP/IP. Such communication error checking is performed in the wireless communication unit 48.

In the TCP/IP protocol, user data (for example, the measurement data or the like) taken over from a high-level protocol hierarchy, such as an application layer, is decomposed into small-sized data packets and communication error checking is performed on a packet basis. In the communication error checking of the TCP/IP protocol, objects to be checked are data packets, and whether or not all the user data (measurement data) in the high-level protocol hierarchy are normally transmitted is not the objects to be checked.

Additionally, in the communication error checking of the TCP/IP protocol, in a case where the data packets cannot be received, the processing is ended in a case where the number of requests of retransmission reaches a predetermined number of times simply by requesting the retransmission of the data packets to a transmission source. Thereafter, processing, such as performing notification of transmission results of the data packets, is not performed.

In the device main body 21, the communication control unit 72 performs the communication error checking having the objects to be checked as the measurement data, in a protocol hierarchy (application layer or the like) at a higher level than TCP/IP, separately from the communication error checking in the protocol of such TCP/IP.

A method of communication error checking of the measurement data by the communication control unit 72 is illustrated in FIG. 9. The communication control unit 72 has a determining unit 72A and a notifying unit 72B. The determining unit 72A determines whether or not the measurement data is normally transmitted to the mobile terminal 22. The communication control unit 72 transmits measurement data for one test order as measurement results of the test order via the wireless communication unit 48, for example, in a case where the measurement for one test order is completed.

As illustrated in a measurement data transmission sequence of FIG. 9, in a case where the measurement data is transmitted, first, a communication link is established between the wireless communication unit 48 of the device main body 21 and the wireless communication unit 54 of the mobile terminal 22. The establishment of the communication link is performed, for example, in a case where the wireless communication unit 48 of the device main body 21 transmits a beacon signal in accordance with a protocol of a wireless LAN and the wireless communication unit 54 of the mobile terminal 22 responds to the beacon signal. In this case, the communication control unit 72 also performs the determination of the access authority of the mobile terminal 22 on the basis of the terminal management information.

In a case where the communication link is established, the communication control unit 72 starts the transmission processing of the measurement data. The communication control unit 72 transmits the measurement data of the plurality of measurement items included in the measurement results of one test order for each measurement item.

In the present example, the measurement data, such as "GLU", "TCHO", "CRE", and "ALB", are included in the measurement results of the one test order. The communication control unit 72 first transmits the measurement data (GLU) of a first measurement item. The mobile terminal 22 receives the measurement data (GLU) in the wireless communication unit 54. Then, the mobile terminal 22 counts received data size (reception data size) as a reception result of the measurement data, and transmits the notification of the counted reception data size to the device main body 21.

In the communication control unit 72, the determining unit 72A determines whether or not the notification of the reception data size is received, the reception data size, and the transmission data size of the measurement data (GLU) transmitted from the device main body 21 are collated with each other, and the measurement data (GLU) is normally transmitted. In a case where the reception data size and the transmission data size coincide with each other, the determining unit 72A determines that normal transmission is made, and in a case where the reception data size and the transmission data size do not coincide with each other, the determining unit 72A determines that the non-transmitted data is generated. The determining unit 72A records a transmission result that is determined regarding the measurement data (GLU) of the first measurement item.

In a case where the transmission of the measurement data (GLU) of the first measurement item ends, the measurement data (TCHO) of a second measurement item is transmitted. It is also determined whether a second piece of measurement data (TCHO) is normally transmitted in the same procedure as above, and a transmission result is recorded. The communication error checking is also similarly performed regarding the measurement data ("CRE", "ALB", . . . ) after a third piece of measurement data, and respective transmission results are recorded.

In the present example, since the first and second pieces of measurement data ("GLU" and, "TCHO") are normally transmitted, the transmission results of these pieces of measurement data are recorded as "Normal". On the other hand, regarding, third and fourth pieces of measurement data ("CRE" and "ALB"), a communication failure occurs during transmission, and these third and fourth pieces of measurement data are not normally transmitted. For that reason, the transmission results of these pieces of measurement data are recorded as "Non-transmitted". In this way, information on whether or not these pieces of measurement data are normally transmitted is included in the transmission results for each piece of measurement data.

The notifying unit 72B notifies the mobile terminal 22 of the recorded transmission results or the diagnosis and treatment department terminal 13 of the requester for testing. The notifying unit 72B notifies the mobile terminal 22 of the transmission results in a case where the non-transmitted data is generated due to a communication failure between the notifying unit 72B and the mobile terminal 22 and in a case where the communication failure is recovered. The notifying unit 72B notifies the diagnosis and treatment department terminal 13 of the transmission results through the wired communication unit 49 in a case where the communication failure between notifying unit 72B and the mobile terminal 22 is not recovered.

Figure 10:
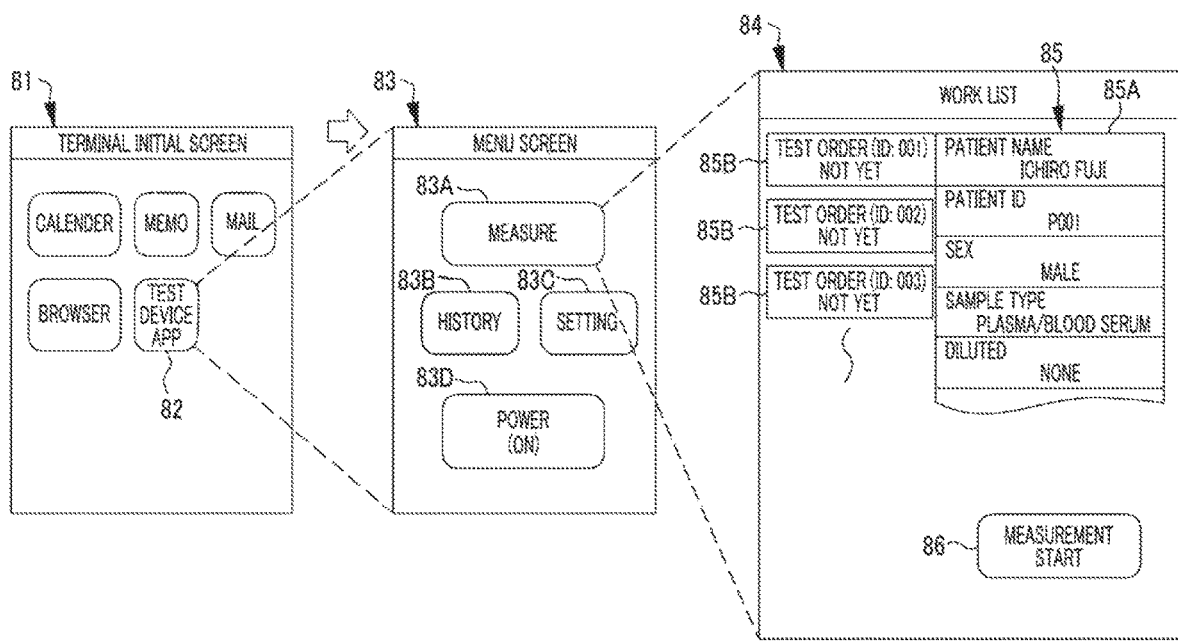
FIG. 10 is an explanatory view of an operation screen of a mobile terminal.

Operation screens of the mobile terminal 22 are illustrated in FIGS. 10 to 13. As illustrated in FIG. 10, in an initial screen 81 of the mobile terminal 22, an icon 82 ("test device application") that starts the test device application program that operates the device main body 21 is displayed as one of icons 82 of various application programs, such as an e-mail, a browser, a calendar, and a memo pad. In a case where the icon 82 is operated in the initial screen 81, a menu screen 83 of the test device is displayed on the touch panel 22A.

The menu screen 83 is provided with a measurement selection button 83A, a history button 83B, a setting button 83C, and a power button 83D. The measurement selection button 83A is a button that selects a measurement menu that is a main menu of the test device 10. In a case where the measurement selection button 83A is operated, a shift to the worklist screen 84 that displays a test order registered in the device main body 21 is made.

The history button 83B is an operation button for displaying history information. In addition to a past measurement history and a past communication history, an operation history showing what kind of operation is performed or the like is included in the history information. For example, information an input path of an operation instruction, such as whether the measurement start instruction is input by the operation of the start switch 28 of the device main body 21 or is input by the operation of the mobile terminal 22, is also included in the operation history. Such an operation history is used for, for example, trouble analysis or the like in a case where some kind of trouble occurs. The setting button 83C is used in order to perform various kinds of setting. In a case where the setting button 83C is operated, a shift to a setting screen is made.

The power button 83D is a button for inputting electric power. The device main body 21 is provided with a main power switch (not illustrated), and the power source of the device main body 21 can be turned on and off by the operation of the power button 83D in a state where the main power switch is turned on. Whether or not the power source is turned on or turned off is displayed on the power button 83D. A state where the power source is turned on ("ON") is illustrated in FIG. 10.

The worklist screen 84 is provided with an order display region 85 where the registered test orders are displayed. The order display region 85 has a contents display region 85A where the contents of the test orders are displayed, and tabs 85B for selecting the test orders. Information, such as doctor names of requesters, diagnosis and treatment departments to which doctors belong, and request days, in addition to test order IDs, patient's names, patient IDs, patient's sexes, sample types, and the need for dilution of samples, is included as the contents of the test orders. These are displayed on the contents display region 85A.

Display of the contents of a plurality of test orders is switched by selecting the tabs 85B on which the test order IDs ("001", "002", and "003") are displayed. In FIG. 10, a tab 85B whose test order ID is "001" is selected, and the contents of the selected test order (ID: 001) are displayed on the contents display region 85A.

In a case where the worklist screen 84 is displayed, the mobile terminal 22 makes an access to the device main body 21 and acquires the test orders registered in the storage 62 of the device main body 21. Then, the acquired test orders are displayed on the worklist screen 84.

The worklist screen 84 is provided with a measurement start button 86. In a case where the measurement start button 86 is operated, test including preprocessing and measurement is started in the procedure illustrated in FIG. 5 regarding the registered test orders registered.

In addition, in a case where the measurement start button 86 is operated, the remaining battery level of the mobile terminal 22 becomes lower. Thus, in a case where a battery is not held by the end of the test, a warning message that the test cannot be continued may be displayed because the remaining battery level is low.

Figure 11:
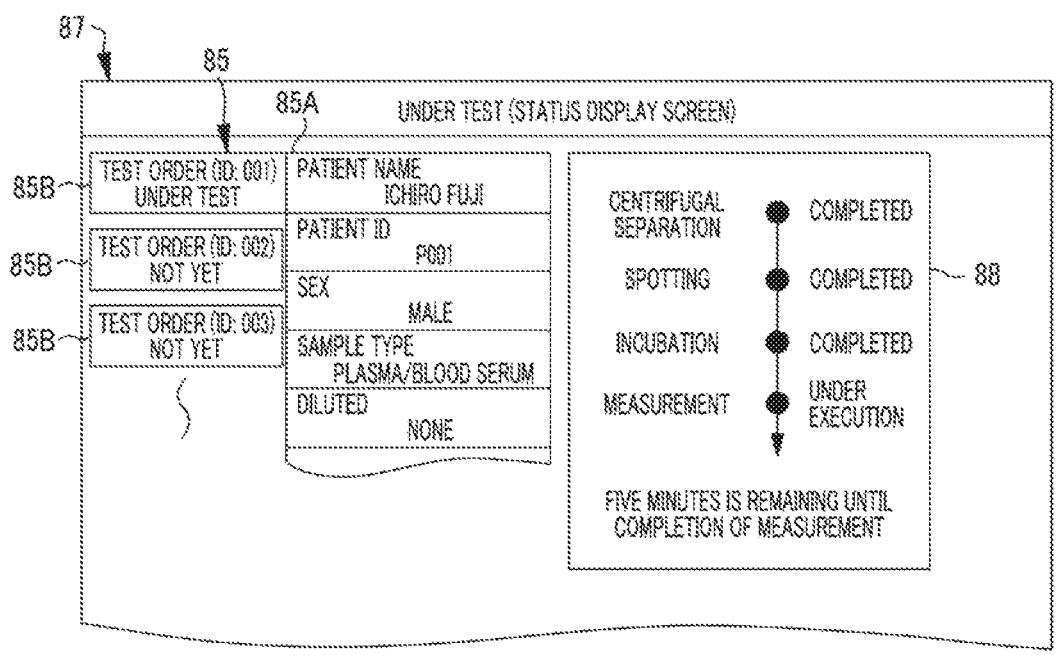
FIG. 11 is an explanatory view of a status display screen.

In a case where the test is started, as illustrated in FIG. 11, a shift to a status display screen 87 that displays the status of the test is made. The status display screen 87 is also provided with the order display region 85, and a status display region 88 is provided beside the order display region 85. A progress status of the test that is currently under execution is displayed on the status display region 88. Specifically, at which level the current level is among respective progress levels of the test, such as centrifugation, spotting, incubation, and measurement, is displayed. The example of FIG. 11 displays that the testing of the test order whose ID is 001 is under execution, the centrifugation, the potting, and the incubation are completed, and the measurement is under execution.

Additionally, the remaining time until the measurement is completed is displayed on the status display region 88. The remaining time is counted down according to the lapse of time. How long it takes to complement the measurement can be confirmed by such remaining time display.

Additionally, a display ("under test") indicating that the test is under execution with respect to the test order (ID: 001) for which the test is under execution is made on the tab 85B, and a display ("Non") indicating that the test is not executed with respect to test orders (ID: 002 and 003) for which the test is not executed is made.

Figure 12:
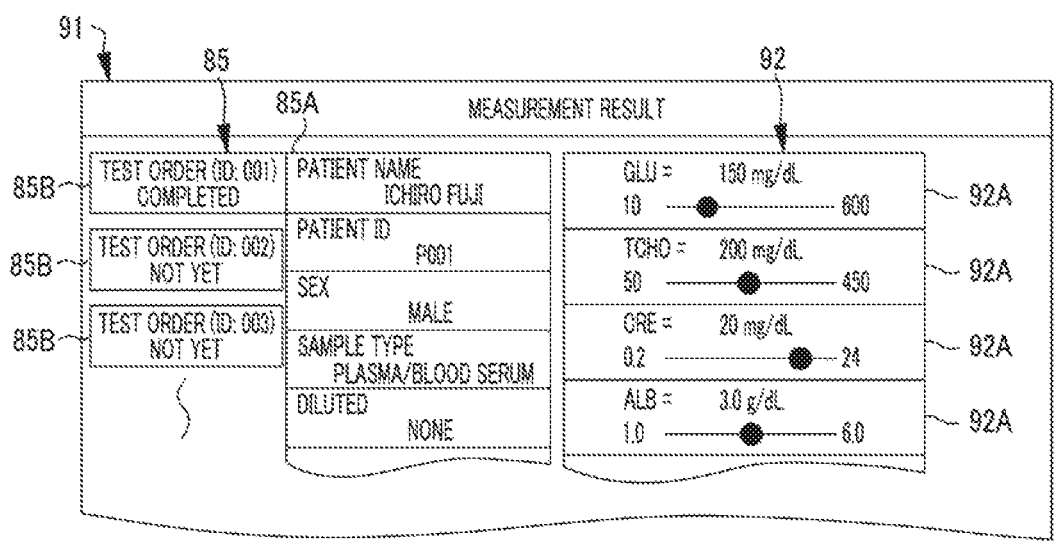
FIG. 12 is an explanatory view of a measurement result display screen.

In a case where the measurement is completed as illustrated in FIG. 12, the measurement result display screen 91 is displayed. The measurement result display screen 91 is provided with the order display region 85 and a measurement result display region 92. Measurement results of a test order selected by a tab 85B of the order display region 85 are displayed on the measurement result display region 92. In the present example, the tab 85B whose test order ID is "001" is selected, and measurement results thereof are displayed.

Measurement data of the plurality of measurement items (GLU, TCHO, CRE, ALB, . . . ) included in one test order is displayed on the measurement result display region 92. The measurement result display region 92 is partitioned into sub-regions 92A that displays the respective measurement items, and each sub-region 92A is allocated to each measurement item.

In addition to values of measurement data of a measurement item, a scale indicating a proper range, and marks that display the positions of the values of the measurement data on the scale are displayed on each sub-region 92A. For example, in the case of the measurement item (GLU), 150 mg/dL is displayed as a value of measurement data within the sub-region 92A. In addition, the scale of 10 mg/dL to 600 mg/dL indicating a proper range is displayed, and a mark indicating the position of 150 mg/dL that is the value of the measurement data on the scale is displayed. The same applies to the sub-regions 92A of the other measurement items (TCHO, CRE, and ALB).

Figure 13:
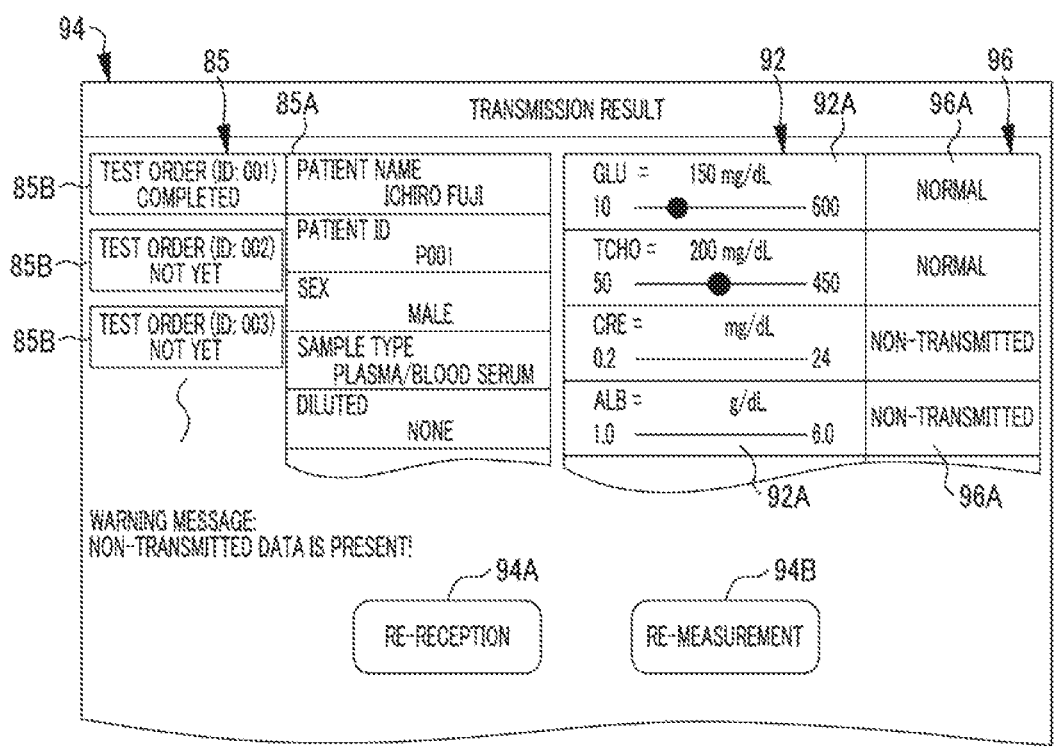
FIG. 13 is an explanatory view of a transmission result display screen.

The transmission result display screen 94 illustrated in FIG. 13 is a screen that displays the transmission results of which the notifying unit 72B of the device main body 21 has notified the mobile terminal 22. The transmission result display screen 94 has a transmission result display region 96 in addition to the order display region 85 and the measurement result display region 92.

Transmission results as to whether the measurement data of the respective measurement items are normally transmitted are displayed on the transmission result display region 96. The transmission results illustrated in FIG. 13 show, as illustrated in FIG. 9, a case where the measurement data of the measurement items (GLU and TCHO) is normally transmitted, but the measurement data of the measurement items (CRE and ALB) is not transmitted.

In this case, regarding the measurement items (GLU and TCHO), "Normal" is displayed on the sub-regions 96A of the transmission result display region 96. Additionally, the values of the measurement data are displayed on the sub-regions 92A of the measurement items (GLU and TCHO).

On the other hand, the measurement items (CRE and ALB) that are not transmitted, "Non-transmitted" is displayed on the sub-regions 96A. Additionally, though natural, on the sub-regions 92A of the measurement items (CRE and ALB), values of measurement data are not displayed, but only scales indicating proper ranges are displayed.

In this way, in the transmission result display screen 94, transmission results are displayed for each measurement item. For that reason, as in the present example, even in a case where some measurement items are normally transmitted but some are not transmitted data, the non-transmitted data can be clearly confirmed. In addition, display modes of the transmission results may be displayed by colors or marks in addition to being displayed as alphabetic information ("Normal") or ("Non-transmitted") as in the present example.

Additionally, a warning message "there is non-transmitted data" is displayed on the transmission result display screen 94. Moreover, since the transmission result display screen 94 has high importance in notification to the test technician T, a preferential display is performed. Specifically, in a case where the mobile terminal 22 receives the notification of the transmission results, a preferential display, such as making the touch panel 22A display in a pop-up manner on another screen under display or automatically switching from another screen to the transmission result display screen 94, is performed. Accordingly, the test technician T can be quickly notified of the transmission results.

In addition, in a case where all the transmission results are normal, the importance of the notification of the transmission results is low. Therefore, only in a case where there is non-transmitted data, the preferential display of the transmission result display screen 94 may be performed.

Additionally, a re-reception button 94A and a re-measurement button 94B are displayed on the transmission result display screen 94. In a case where the re-reception button 94A is operated, re-reception of the measurement data is requested to the mobile terminal 22 and the device main body 21. In a case where the device main body 21 receives the re-reception request, the measurement data that has been the non-transmitted data is retransmitted again to the mobile terminal 22. In addition, as a method of the retransmission, only the measurement data that has been the non-transmitted data may be retransmitted, or all the measurement data for one test order including the non-transmitted data may be retransmitted.

The re-measurement button 94B is an operation button for requiring not only the retransmission of the measurement data but also re-measurement. Even regarding the measurement data whose transmission results are regarded as normal, in a case where the values of the measurement data indicate abnormal values that are not normally assumed, there may be a case where an operation error under measurement is considered to be the cause. In such a case, it is necessary to request the re-measurement from the device main body 21. In a case where the re-measurement is requested to the device main body 21 by the operation of the re-measurement button 94B, the device main body 21 executes the re-measurement and the retransmission of re-measurement results.

The operation of the above configuration will be described referring to flowcharts of FIGS. 14 and 15. The doctor D of the diagnosis and treatment department 12 issues a test order with the diagnosis and treatment department terminal 13 in a case where the doctor D diagnoses a patient and admits that there is a need for test. The test order issued in the diagnosis and treatment department terminal 13 is transmitted to the device main body 21 via the in-hospital LAN 14. The device main body 21 registers the test order in the storage 62 in a case where the device main body 21 receives the test order (S(Step)1010).

In a case where the new test order is registered, the device main body 21 notifies the mobile terminal 22 of that fact. Through this notification, the test technician T can confirm that the new test order has been registered. In a case where the measurement selection button 83A is operated from the menu screen 83, the worklist screen 84 illustrated in FIG. 10 is displayed. In a case where the worklist screen 84 is displayed, an access is made to the device main body 21 from the mobile terminal 22, and order information within the storage 62 is acquired. Accordingly, the new test order is displayed on the worklist screen 84 of the mobile terminal 22 (S2010).

The test technician T confirms the contents of the test order, and prepares a sample and a cartridge 18 that is a target to be tested. Then, the sample is contained in the sample container 16. The device main body 21 is loaded with a sample set having the sample container 16 and the cartridge 18 as one set (S1020). The work of loading such a sample set is performed for four sets to the maximum in accordance to the number of test orders.

Additionally, in the case of the work of loading the sample set, a calibration card 33 attached to an analysis slide 17 of the cartridge 18 to be used is passed through the slit 32, and calibration information is input to the device main body 21. The device main body 21 executes calibration according to the loaded analysis slide 17 on the basis of the input calibration information.

In a case where the loading of the sample set is completed, the test technician T operates the measurement start button 86 in the worklist screen 84 of the mobile terminal 22. Accordingly, a measurement start instruction is transmitted from the mobile terminal 22 (S2020). The device main body 21 starts test including preprocessing and measurement in a case where the measurement start instruction is input (S1030). The test is performed for each test order. The device main body 21 first starts test for one test order (S1040).

In the test, a series of processing including the centrifugation of the sample, the spotting of the sample onto each analysis slide 17, incubation, and measurement is executed in accordance with the procedure illustrated in FIG. 5. In the case of the sample spotting, an item code of each analysis slide 17 is read by the bar code reader 64. Then, a correspondence relationship between the position of the analysis slide 17 on the plate 46A of the incubator 46 and the item code is recorded in the storage 62. On the basis of this correspondence relationship, measurement data for each measurement item is recorded.

Additionally, the device main body 21 notifies a progress status of the test under execution to the mobile terminal 22. The progress status is displayed on the status display screen 87 illustrated in FIG. 11. The test technician T can confirm the progress status and the remaining time of the current test by the status display screen 87.

In the device main body 21, measurement is performed by the measuring part 47 for each analysis slide 17 in a case where the incubation is completed. In a case where the measuring part 47 executes the measurement regarding one measurement item (S1050), the measuring part 47 outputs measurement data of the executed measurement item (S1060). The output measurement data is stored in storage 62. In a case where there is the next measurement item, the next analysis slide 17 is measured and measurement data is output (S1070). The measurement data obtained by measuring each analysis slide 17 is matched and recorded for each measurement item within the storage 62.

In a case where the measurement of the measurement items for one test order ends (S1080), transmission processing of the measurement data for one test order is performed (S1090). Accordingly, reception processing of the measurement data transmitted from the device main body 21 is performed in the mobile terminal 22 (S2030).

Figure 15:
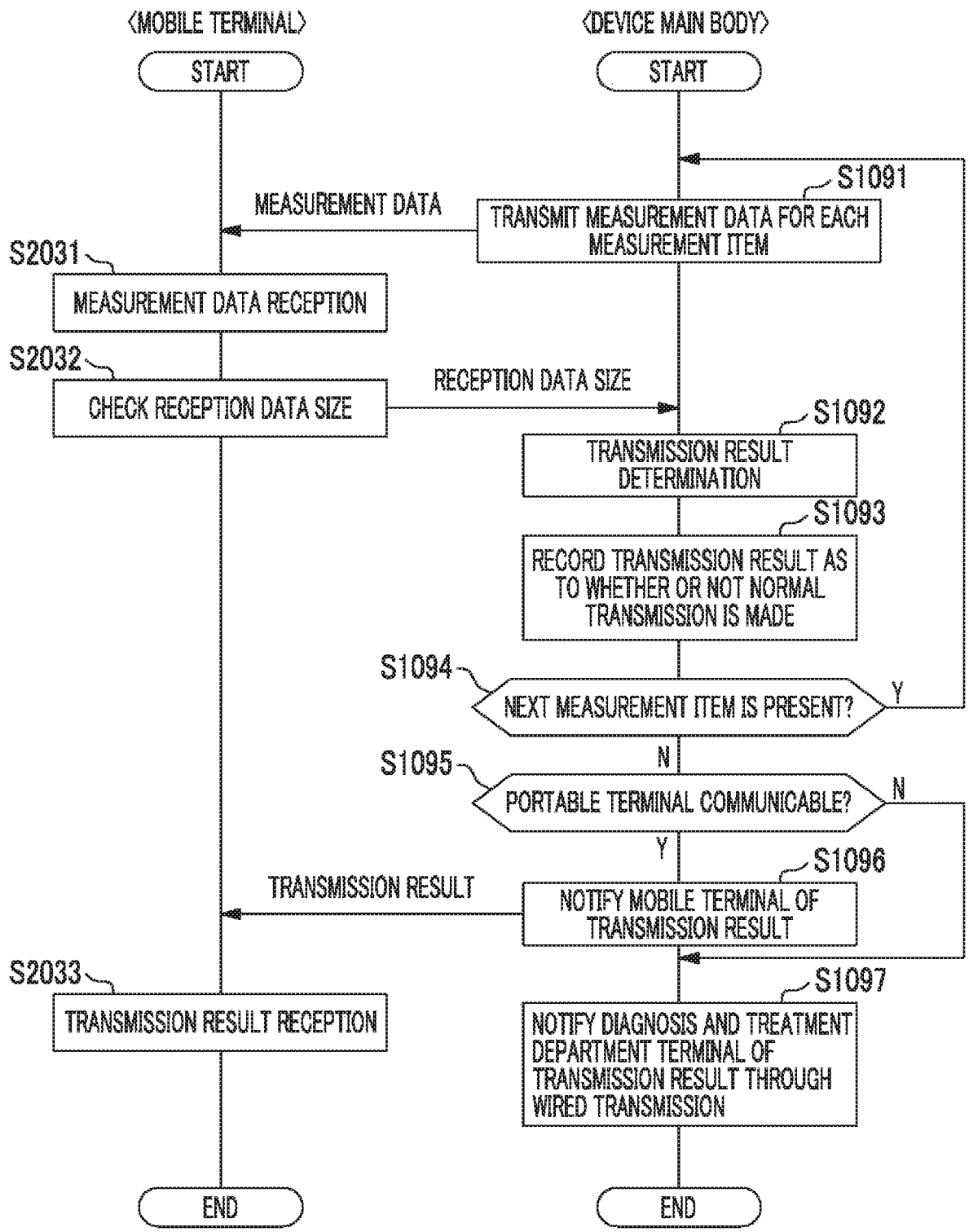
FIG. 15 is a flowchart for transmission and reception processing of the measurement data.

Such transmission and reception processing (S1090 and S2030) of the measurement data for one test order is performed in a procedure illustrated in FIG. 15. First, the device main body 21 transmits the measurement data for each measurement item (S1091). The mobile terminal 22 receives the measurement data (S2031) to check a reception data size regarding the measurement data (S2032). The mobile terminal 22 transmits the reception data size to the device main body 21.

In the device main body 21, in a case where the reception data size is received, the determining unit 72A collates the reception data size with a transmission data size to determine a transmission result (S1092). In a case where data sizes of the reception data size and the transmission data size coincide with each other, the determining unit 72A determines that normal transmission is made, and in a case where the data sizes do not coincide with each other, the determining unit 72A determines that non-transmitted data is generated. The determining unit 72A records a determination result as to whether the normal transmission is made as the transmission result (S1093). The determining unit 72A also performs the same processing regarding the measurement data of the next measurement item, and records a transmission result (S1094).

In a case where the recording of the transmission results is completed regarding all the measurement items for one test order (N in S1094), the notifying unit 72B determined whether or not the notifying unit 72B is communicable with the mobile terminal 22 (S1095). In a case where a communication failure between the notifying unit 72B and the mobile terminal 22 is recovered, the notifying unit 72B notifies the mobile terminal 22 of the transmission results (S1095). In a case where the communication failure is not recovered, the diagnosis and treatment department terminal 13 of a requester for the test order is notified of the transmission results through wired communications (S1097). In a case where the communication failure is recovered, the mobile terminal 22 receives the transmission results from the device main body 21 (S2033).

Figure 14:
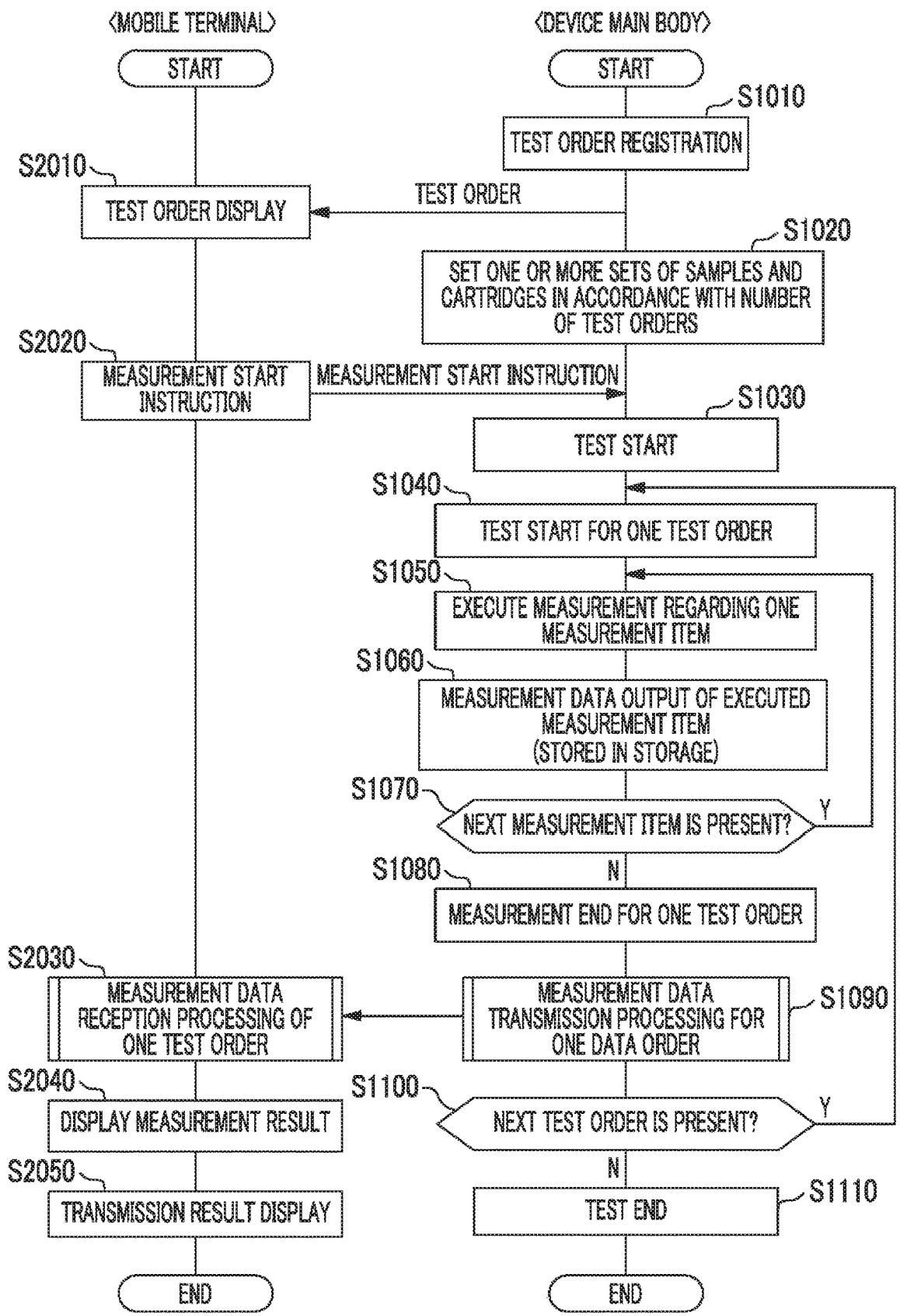
FIG. 14 is a flowchart illustrating a procedure for testing.

In FIG. 14, in a case where the transmission processing of the measurement data for one test order is completed (S1090), the device main body 21 starts the processing of the next test order (Y in S1100). In a case where there is no next test order (N in S1110), the test is ended (S1110).

In a case where the mobile terminal 22 receives the measurement data (S2030), the mobile terminal 22 displays the measurement data on the touch panel 22A as the measurement results (S2040). The measurement results are displayed on the measurement result display screen 91 illustrated in FIG. 12. Then, in a case where the mobile terminal 22 receives the transmission results, the mobile terminal 22 displays the transmission results on the touch panel 22A (S2050). The transmission results are displayed on the transmission result display screen 94 illustrated in FIG. 13.

In a case where the test technician T confirms that all the measurement data are normally transmitted in the transmission result display screen 94, the test technician T transmits the notification of the completion of test to the doctor D of the diagnosis and treatment department 12 of the requester. The measurement results are transmitted from the device main body 21 via the in-hospital LAN 14 to the diagnosis and treatment department terminal 13.

Additionally, in a case where there is non-transmitted data due to the communication failure, a display or a warning message indicating that there is non-transmitted data is displayed on the transmission result display screen 94. The test technician T can confirm that there is non-transmitted data from the transmission result display screen 94. Accordingly, overlooking of the non-transmitted data is prevented. In a case where there is non-transmitted data, the re-reception button 94A of the transmission result display screen 94 is operated, and an instruction for retransmission of the measurement data is provided to the device main body 21. Additionally, the re-measurement button 94B is operated if necessary, and an instruction for re-measurement is provided.

Since wireless communication with a larger occurrence frequency of communication failures compared to wired communication is performed between the device main body 21 and the mobile terminal 22, a communication error-checking function by the communication control unit 72 and a notification function of the transmission results to the mobile terminal 22 have particularly high needs.

Moreover, information ("Normal" or "Non-transmitted") as to whether or not respective pieces of measurement data of the plurality of measurement items are normally transmitted included in the transmission results that are notified of from the device main body 21 and displayed on the transmission result display screen 94 of the mobile terminal 22. For that reason, it is possible to clearly confirm not only the presence/absence of non-transmitted data but also that measurement data of a certain measurement item is normally transmitted, or conversely, that measurement data of a certain measurement item is not transmitted. Additionally, it is also possible to clearly confirm the number of pieces of the non-transmitted data.

The device main body 21 can collectively measure a plurality of measurement items regarding one test order for one sample by using the cartridge 18 having a plurality of analysis slides 17 corresponding to the plurality of measurement items. The measuring part 47 that constitutes the test unit 42 outputs measurement data relating to the plurality of measurement items in the testing of the one sample. Under the control of the communication control unit 72, the wireless communication unit 48 wirelessly transmits a plurality of pieces of measurement data regarding the plurality of measurement items output in this way to the mobile terminal 22.

In this way, in a case where the measurement data of the plurality of measurement items is transmitted with respect to the one test order, it is highly necessary to know information, such as the measurement data to which has been normally transmitted and the measurement data from which is non-transmitted data. This is because, in a case where only the measurement data of one measurement item is transmitted, it is natural that the number of objects to be transmitted is one; therefore, it is only necessary to confirm whether or not the measurement data is not transmitted and there is no need to confirm the number of pieces and the contents of non-transmitted measurement data.

Since all the plurality of measurement items measured in accordance with the test order are important measurement items used for diagnosis, there should be no missing in the measurement items. For that reason, as in the device main body 21, in a device that outputs the measurement data of a plurality of measurement items in the testing of one sample and wirelessly transmits these pieces of measurement data, it is very useful to provide notification of a transmission result for each measurement data.

Additionally, in the present example, the measuring part 47 that constitutes the test unit 42 outputs the measurement data of the plurality of measurement items regarding the one sample. However, even in a case where only the measurement data of the one measurement item regarding the one sample is output, the present invention is useful for a device that continuously processes a plurality of test orders as in the device main body 21.

This is because, even in a case where the measurement data of one measurement item is output for each sample in the device main body 21, the measuring part 47 outputs a plurality of pieces of measurement data for each sample in a case where a plurality of different samples are tested. Even in a case where such a plurality of pieces of measurement data are transmitted, it is preferable that a transmission result can be confirmed for each sample. For that reason, as in the device main body 21, in a device that outputs wirelessly transmits a plurality of pieces of measurement data, it is very useful to provide notification of the transmission result for each measurement data for each sample.

Additionally, even in a case where the mobile terminal 22 cannot be notified of the transmission result, the notifying unit 72B notifies the diagnosis and treatment department terminal 13 of the requester of the transmission result through wired communication. For that reason, even in a case where the mobile terminal 22 is not notified of the transmission result and the test technician T cannot confirm the presence of non-transmitted data, the doctor D of the requester can confirm the transmission result. Thus, overlooking of the non-transmitted data can be reliably prevented.

Additionally, the determining unit 72A of the device main body 21 receives the notification of a reception data size as a reception result from the mobile terminal 22 after the measurement data is transmitted, and determines whether or not the measurement data is normally transmitted on the basis of the reception data size. In this way, since transmission determination is in the device main body 21 that is a transmission source of the measurement data, determination accuracy is high. This is based on the following reason.

That is, as in the mobile terminal 22, in a case where a general-purpose tablet terminal is used, the degree of freedom in design, such as designing of specifications, is poor as compared to the device main body 21 developed as a dedicated device. For that reason, in the mobile terminal 22, there may be a case where the performance for realizing required determination accuracy cannot be secured. On the contrary, since the device main body 21 is developed as a dedicated device, it is easy to secure the performance for realizing required determination accuracy.

Additionally, since the notification of a reception result is received from the mobile terminal 22 of the transmission destination and the transmission determination is performed by the device main body 21 of the transmission source, transmission determination for each measurement data can be simply performed. This is because the device main body 21 has the measurement data to be transmitted; therefore, the data size of measurement data to be transmitted can be simply ascertained. For that reason, in a case where the notification of the reception result, such as the reception data size, can be received from the mobile terminal 22, the collation between the reception data size and the data size of the measurement data is possible, and the transmission determination can be simply performed.

In addition, another method may be used as the method for the transmission determination. For example, the data size of the measurement data to be transmitted is recorded to the header information of the measurement data that the device main body 21 transmits. In the mobile terminal 22, the data size read from the header information of the received measurement data and the reception data size are collated with each other. Then, a collation result as to whether the data sizes coincide with each other is transmitted as a reception result from the mobile terminal 22 to the device main body 21. In the device main body 21, the determining unit 72A performs the transmission determination on the basis of the received collation result.

However, in the method of collating the data sizes with each other in the mobile terminal 22 in this way, compared to a case where the data sizes are collated with each other in the device main body 21, the processing of the mobile terminal 22 becomes complicated, and the load of the processing becomes large. For that reason, since it is difficult to adopt this method in the mobile terminal 22 in which the degree of freedom in design is poor, it is preferable to perform the collation in the device main body 21 as shown in the above example.

Additionally, since a reception result of which the device main body 21 is notified from the mobile terminal 22 is used as the reception data size, the mobile terminal 22 may perform the processing of counting the data size and the complicated processing of the mobile terminal 22 is unnecessary. For that reason, the processing load of the mobile terminal 22 is suppressed.

Additionally, although an example in which the mobile terminal 22 functions as the operation terminal of the device main body 21 has been described, the mobile terminal 22 may not have the function of the operation terminal, and may have at least the function of browsing the measurement data. However, in a case where the mobile terminal 22 functions as the operation terminal, it is considered that the frequency with which the test technician T uses the mobile terminal 22 increases. For that reason, it is considered that it is effective notify the mobile terminal 22 of the transmission results in order to call the test technician's T attention regarding the non-transmitted data, compared to a case where the mobile terminal 22 does not function as the operation terminal.

In addition, although an example in which the transmission results including the information on whether or not the measurement data is normally transmitted for each measurement item has been described in the present example, at least the presence of the non-transmitted data may be included in the transmission results. Of course, as described above, it is preferable to allow the transmission results to be identified for each measurement item.

Additionally, in the present example, not only in a case where there is non-transmitted data but in a case where normal transmission is made, the mobile terminal 22 is notified of the transmission results from the device main body 21. However, in a case where normal transmission is made, notification of the transmission results is not provided, and only in a case where there is non-transmitted data, notification of the transmission results may be provided.

Second Embodiment

Figure 16:
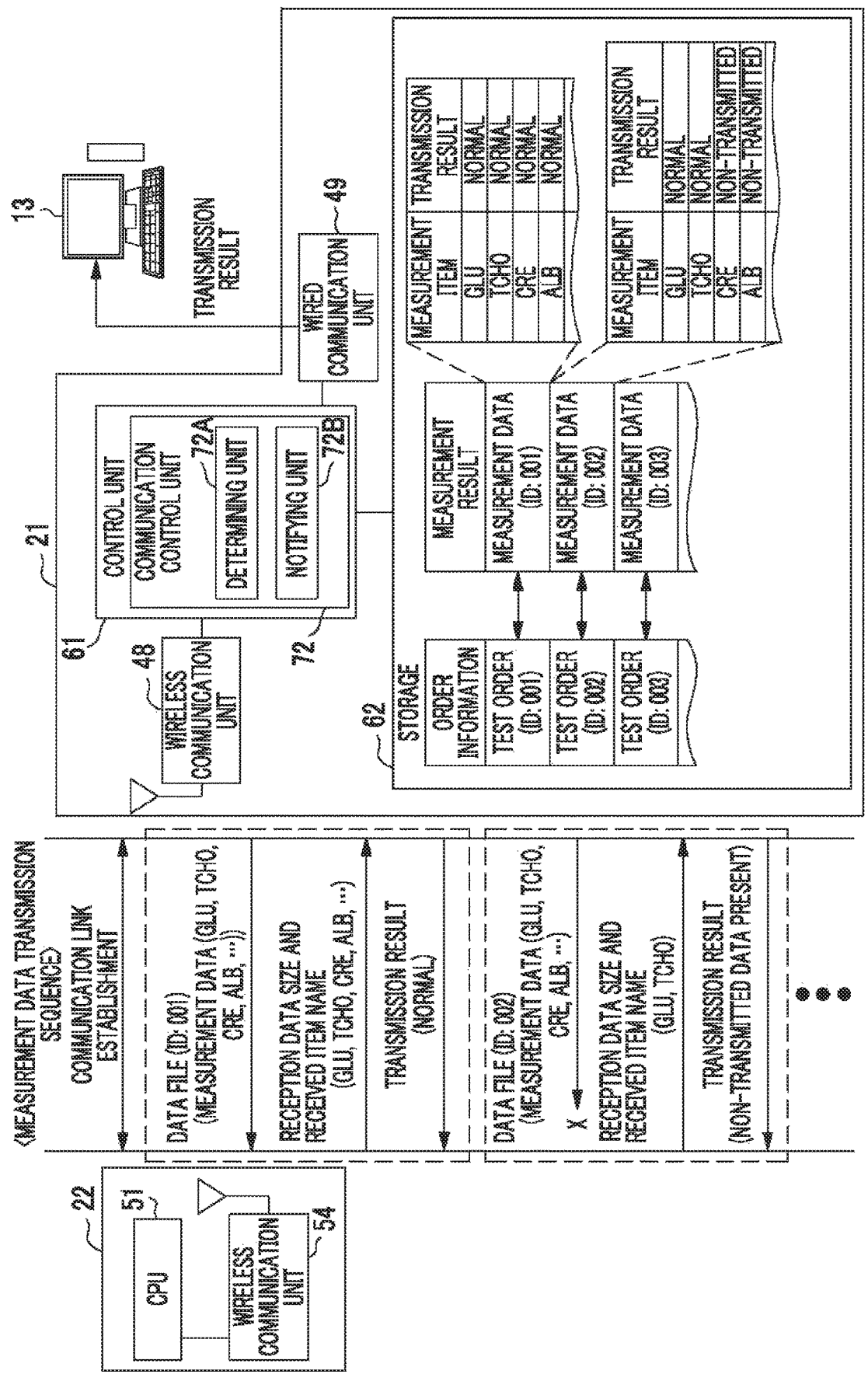
FIG. 16 is an explanatory view of a measurement data transmission sequence of a second embodiment.
Figure 17:
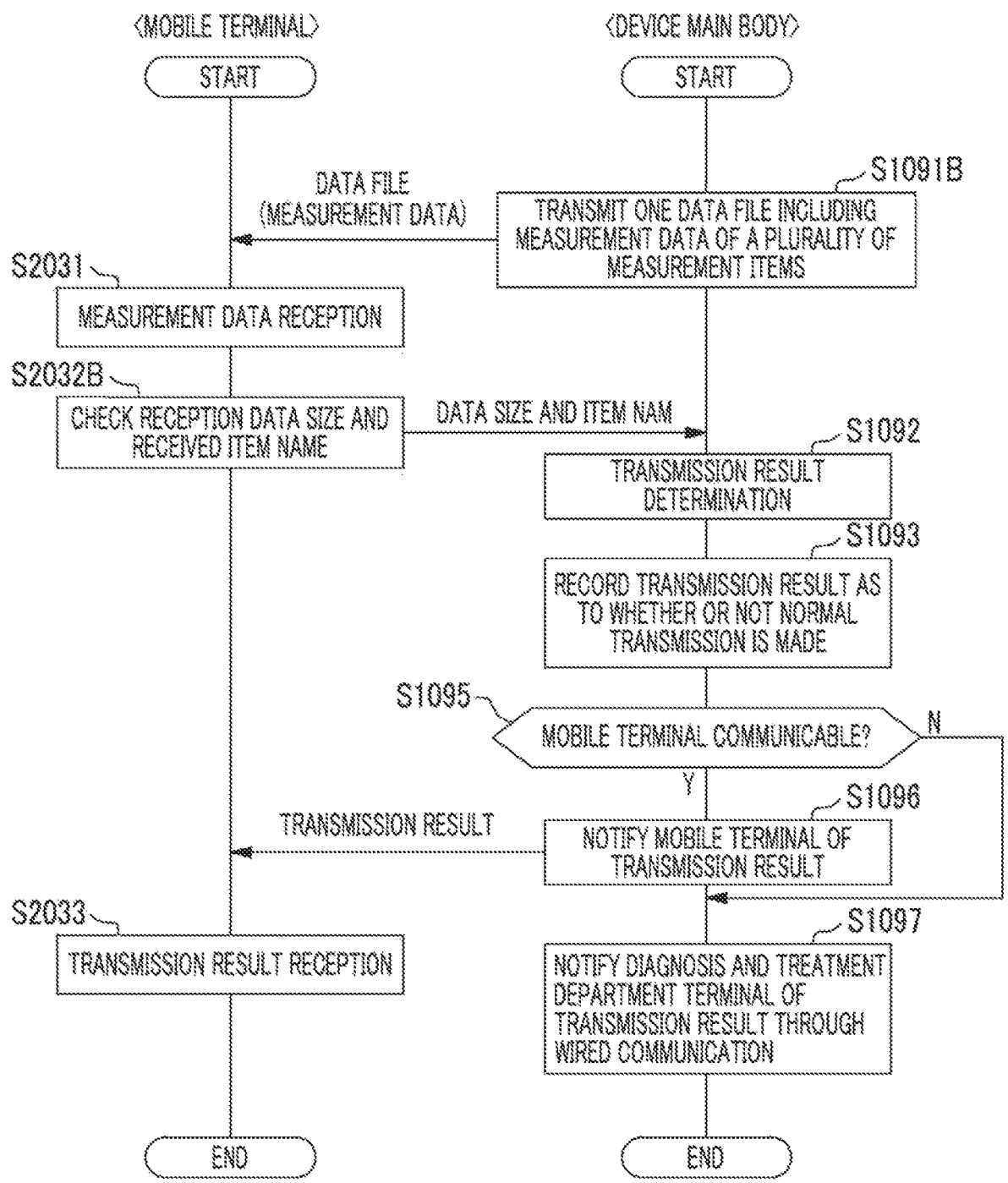
FIG. 17 is a flowchart for measurement data transmission and reception processing of a second embodiment.

A second embodiment illustrated in FIGS. 16 and 17 is an example in which measurement data of a plurality of measurement items are collected in one data file and transmitted. Specifically, in the first embodiment, as illustrated in FIG. 9, the measurement data of the plurality of measurement items (GLU, TCHO, CRE, ALB, . . . ) included in one test order are displayed in units of each recording. In contrast, in the second embodiment, as illustrated in FIG. 16, the plurality of measurement items (GLU, TCHO, CRE, ALB, . . . ) included in one test order are collected in one data file and transmitted.

The data file is, for example, comma-separated values (CSV) format, and is a text file in which item names (GLU, TCHO, CRE, ALB, . . . ) of the respective measurement items and the values (150, 200, . . . ) of respective pieces of measurement data are separated and recorded in commas, respectively.

Transmission and reception processing of the measurement data for one test order is performed in a procedure illustrated in FIG. 17. A difference between the procedure illustrated in FIG. 17 and the procedure of FIG. 15 of the first embodiment is that Step of S1091 is changed to Step of S1091B and Step of S2032 is changed to Step of S2032B, and that Step equivalent to S1094 of FIG. 15 is not present in the procedure of FIG. 17. The others are the same as those of the procedure of FIG. 15.

In a case where the processing of one test order is completed in the device main body 21, the communication control unit 72 wirelessly transmits the measurement data for one test order to the mobile terminal 22 via the wireless communication unit 48. In this case, the communication control unit 72 collects the measurement data of the plurality of measurement items in one data file, and transmits this data file to the mobile terminal 22 (S1091B).

In a case where the mobile terminal 22 receives the data file including the plurality of pieces of measurement data, the mobile terminal 22 checks the reception data size of the data file and the received item names of the measurement items recorded in the data file (S2031). Then, the mobile terminal 22 transmits the reception data size and the received item names to the device main body 21 as reception results (S2032B). Here, the received item names are equivalent to received item information. The received item information may be other than the item names, and may be information capable of specifying the measurement items, such as coded item IDs.

In a case where the plurality of pieces of measurement data are transmitted in one data file, there may be a case where a communication failure occurs during the transmission of the data file and part of the data file is not transmitted. For example, a data file (ID: 002) of a test order whose ID is 002 as illustrated in FIG. 16 shows an example in which a communication failure occurs during the transmission of the data file and the measurement data of two measurement items of GLU and TCHO is normally transmitted but the measurement data of the remaining measurement items are not transmitted.

In this case, the mobile terminal 22 counts the data size of the received data file to obtain the reception data size. Moreover, the item names of the measurement items are read from the received data file. The read item names become the received item names. The reception data size and the received item names are transmitted to the device main body 21 as reception results.

In the device main body 21, on the basis of the reception data size and the received item names, the determining unit 72A determines which measurement items among the measurement data of the plurality of measurement items included in the data file are normally transmitted, and which measurement items become non-transmitted data. The determining unit 72A records determination results of the respective measurement items in the storage 62 as transmission results.

Here, the reason why the reception data size is used in addition to the received item names in the transmission determination is that there may be a case where only the item names are transmitted and the values themselves of measurement data corresponding to the item names are not transmitted. For that reason, even in a case where the received item names are included in the reception results, in a case where it is determined that the values of the measurement data are transmitted on the basis of the reception data size, it is determined that the measurement data of the measurement items are not transmitted.

In this way, the determining unit 72A performs the transmission determination of the measurement data for each measurement item. As illustrated in FIG. 16, with respect to each test order, transmission results are recorded for each measurement item. The example of FIG. 16 is an example in which, regarding the test order whose ID is 001, all the measurement items are normally transmitted, and regarding the test order whose ID is 002, only the measurement items of "GLU" and "TCHO" are normally transmitted and the remaining measurement items are not transmitted.

Modification Example 1

As shown below, it is also possible to add various functions to the test device 10 shown in the above embodiment. Modification Example 1 illustrated in FIGS. 18 and 19 includes an error notification function of providing notification of the contents of various errors in a case where the errors occur the device main body 21. Here, the errors of Modification Example 1 are not limited to a communication error, and include various errors, such as a measurement error, a bar code reading error, and malfunctions of the centrifugal separation mechanism and the spotting mechanism.

Figure 19:
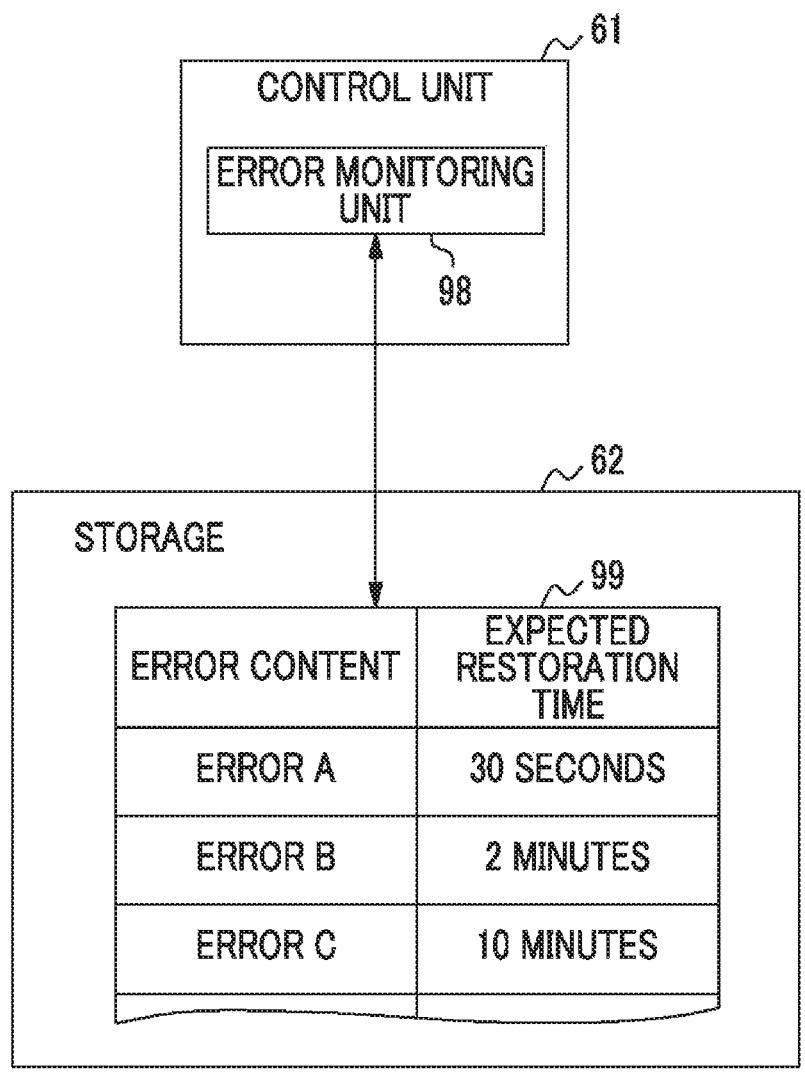
FIG. 19 is an explanatory view of a restoration timetable of Modification Example 1.

As illustrated in FIG. 19, in Modification Example 1, the control unit 61 of the device main body 21 is provided with an error monitoring unit 98. Additionally, a restoration timetable 99 in which various errors A, B, and C and respective expected restoration times are recorded in association with each other is stored in the storage 62.

Figure 18:
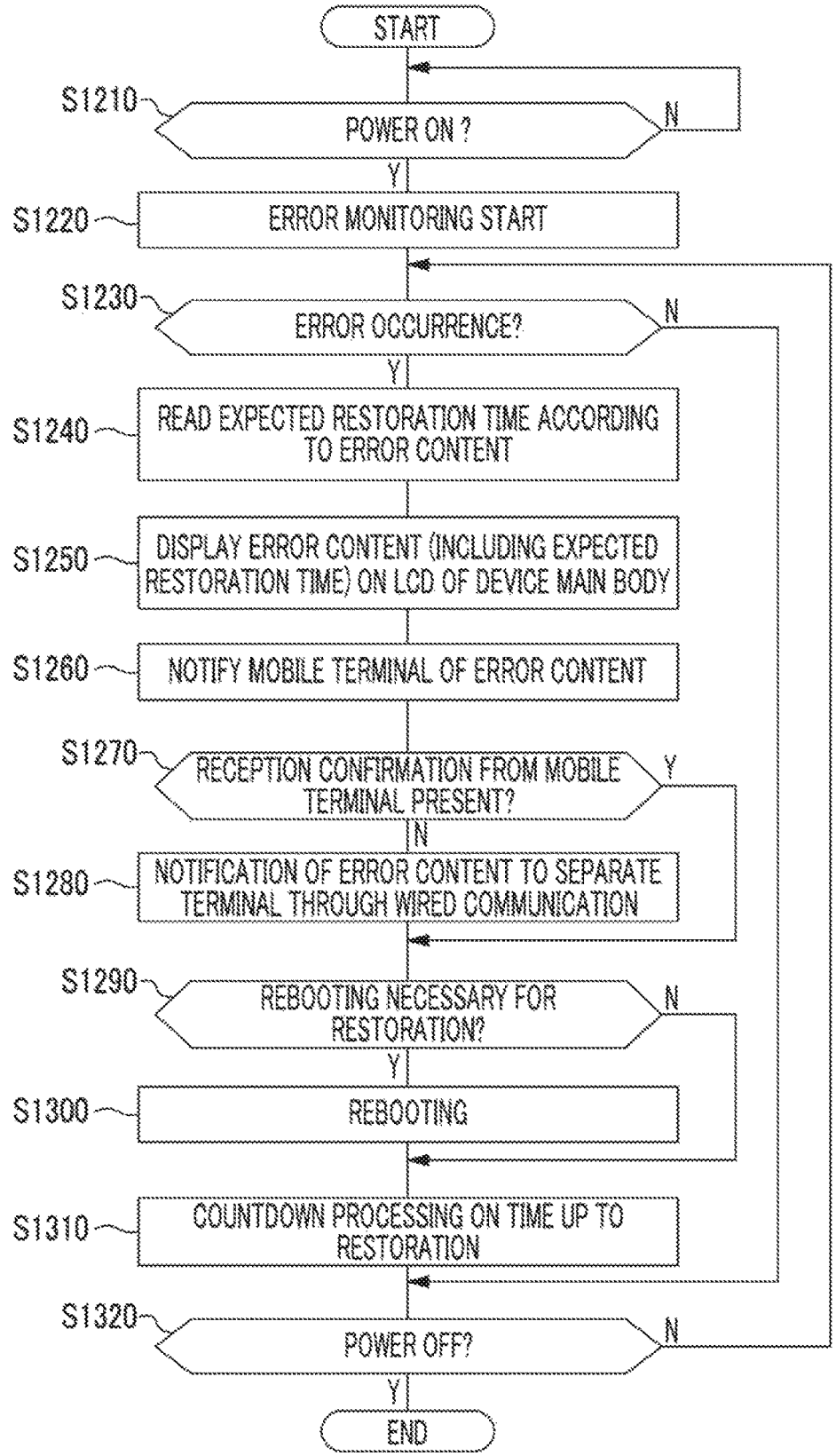
FIG. 18 is a flowchart for error processing of a device main body of Modification Example 1.

As illustrated in a flowchart of FIG. 18, in a case where the power source of the device main body 21 is turned on (Y in S1210), the error monitoring unit 98 monitors starts error monitoring (S1220). In a case where an error occurs (Y in S1230), the error monitoring unit 98 reads an expected restoration time in accordance with the contents of the error from the restoration timetable 99 (S1240). Then, the error monitoring unit 98 displays the contents of the error including the expected restoration time on the LCD 27 of the device main body 21 (S1250). Additionally, the mobile terminal 22 is also notified of the contents of the error (S1260).

Since the wireless communication is performed between the device main body 21 and the mobile terminal 22, there may be a case where notification of the contents of the error is not provided due to a communication failure. For that reason, the error monitoring unit 98 stands by a reception confirmation from the mobile terminal 22 after notification to the mobile terminal 22 (S1270). Then, in a case where there is the notification of the reception confirmation from the mobile terminal 22 (Y in S1270), it is determined that the mobile terminal 22 is notified of the contents of the error.

On the other hand, in a case where there is no notification of the reception confirmation from the mobile terminal 22 (N in S1270), it is determined that the notification of the contents of the error is not provided (N in S1270). In this case, a separate terminal, such as the diagnosis and treatment department terminal 13 is notified of the contents of the error through wired communication or wireless communication (S1280). In addition, in a case where the separate terminal is notified of the contents of the error, it is preferable to further provide notification of a message indicating that the mobile terminal 22 could not be notified of the contents of the error.

The reason why a notification destination of the contents of the error is used as the diagnosis and treatment department terminal 13 is as follows. The doctor D of the requester for testing often stands by the end of the requested test, and is highly interested in the end time of the test. For that reason, in a case where an error occurs in the device main body 21 and the end of the test is delayed more than expected, there is an effect of alleviating a doctor's D mental burden by quickly delivering this message through the notification of the contents of the error.

The error monitoring unit 98 determines whether or not rebooting is required for restoration in accordance with the contents of the error after notification of the contents of the error (S1290). In a case where the rebooting is required, the rebooting is executed (S1300). Then, the error monitoring unit 98 performs countdown processing on the time up to restoration irrespective of the need for the rebooting (S1310). The countdown processing is performed in all or a part of the notification destination of the contents of the error. For example, the countdown processing may be performed only by the LCD 27 of the device main body 21, or the time for notification to the mobile terminal 22 or the diagnosis and treatment department terminal 13 may be counted down. In a case where the power source is turned off, the error monitoring ends (S1320).

Modification Example 2

Modification Example 2 illustrated in FIGS. 20 to 24 relates to a function of interrupting a test order performed by the order management unit 71. As described above, in a case where the order management unit 71 receives a test order from the requester, the order management unit 71 registers the received test order in the order information within the storage 62. The turn of processing of the registered test order is a registration turn in principle. However, since there is a test order to be preferentially processed irrespective of the registration turn, the order management unit 71 includes a function of interrupting the test order.

Figure 20:
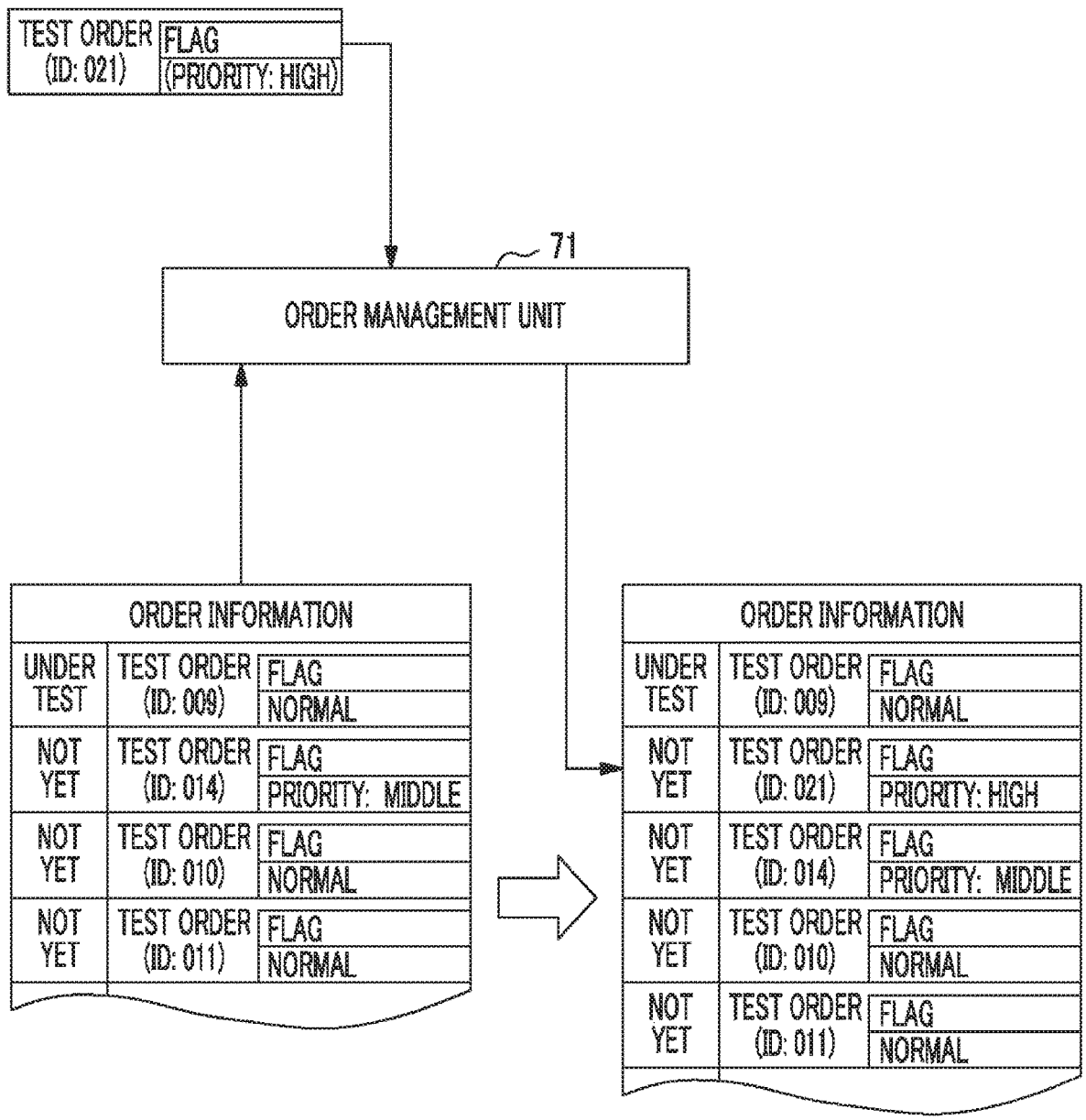
FIG. 20 is an explanatory view of a preferential interruption of Modification Example 2.

An example illustrated in FIG. 20 is an example of a preferential interruption in which an interrupt is made in accordance with the priority of a test order. The priority is set to, for example, a flag accompanying the test order. The priority is set by, for example, a user, such as a doctor or a test technician of a requester of the test order. In FIG. 20, a plurality of test orders whose IDs are 009, 014, 010, 011, . . . is registered in this order in the order information. Among these, a test order whose ID is 009 is being tested. In a test order whose registration turn is second and whose ID is 014, its priority is set to "MIDDLE", and in the other test orders whose registration turns are first, third, and fourth, their priorities are not set and are all normal.

In this status, a case where the order management unit 71 has newly received a test order whose priority, for example, is set to "high" and whose ID is 021 is considered. The newly received test order has the highest priority among the test orders under standby excluding the test order under test. For that reason, the order management unit 71 interrupts and registers the new test order whose priority is "high", in a second position that is an uppermost position among the positions of the test orders under standby.

Figure 21:
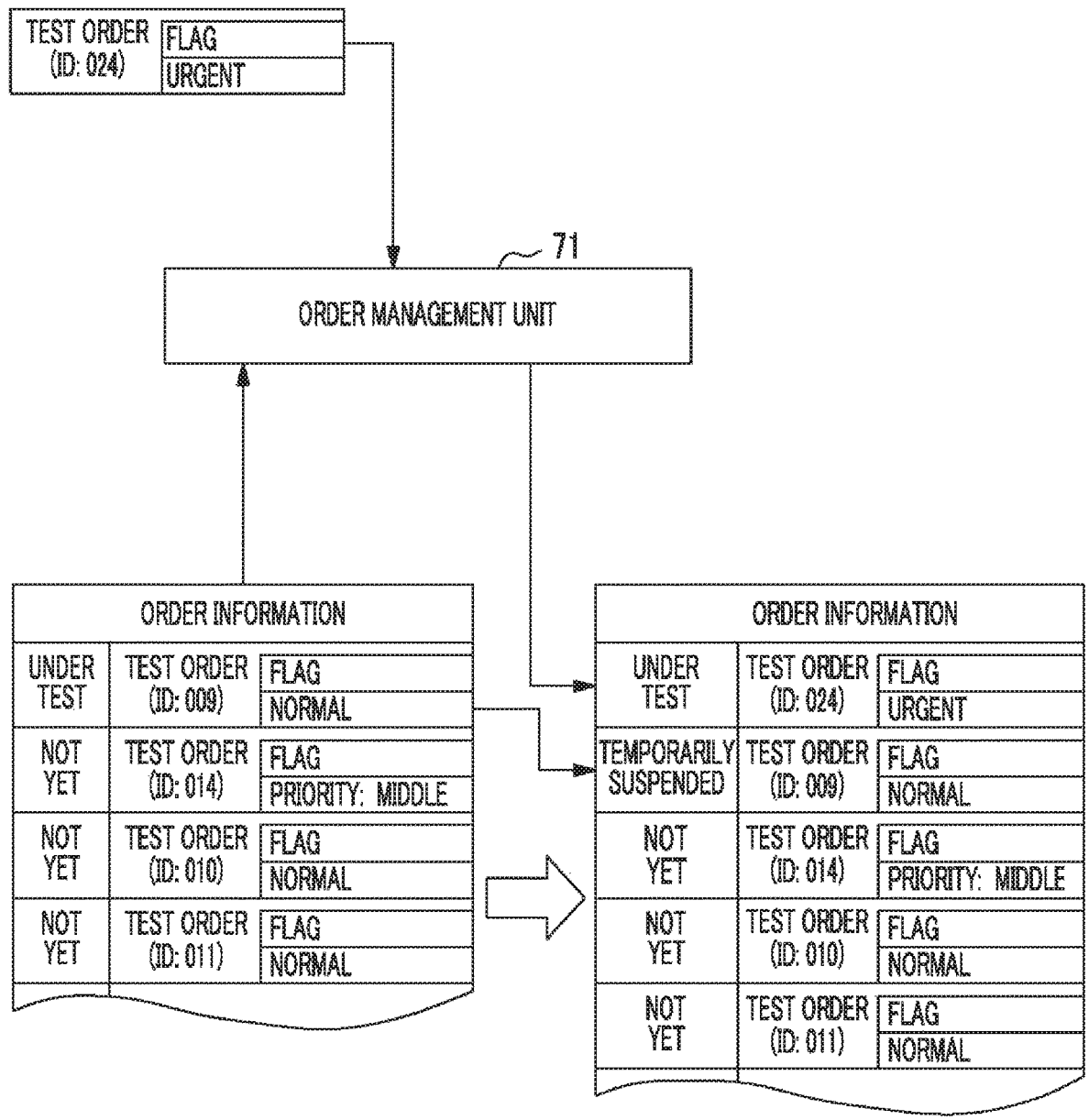
FIG. 21 is an explanatory view of an urgent interruption of Modification Example 2.

The example illustrated in FIG. 21 is an example of an urgent interruption. In the urgent interruption, in a case where there is a test order that is urgently specified, even in a case where there is currently a test order under test, the testing of this test order is temporarily suspended and the urgently specified test order is interrupted in a first position. In FIG. 21, the order information before the execution of interrupt processing is the same as the example of FIG. 20. In a case where the order management unit 71 receives a new test order (ID: 024) that is urgently specified, the order management unit 71 interrupts and resisters the urgently specified test order (ID: 024) in the first position. Then, in a case where the urgently specified test order is registered in the first position, the processing of the test order which is under test and whose ID is 009 suspends temporarily, and the processing of the urgently specified test order is started.

Figure 22:
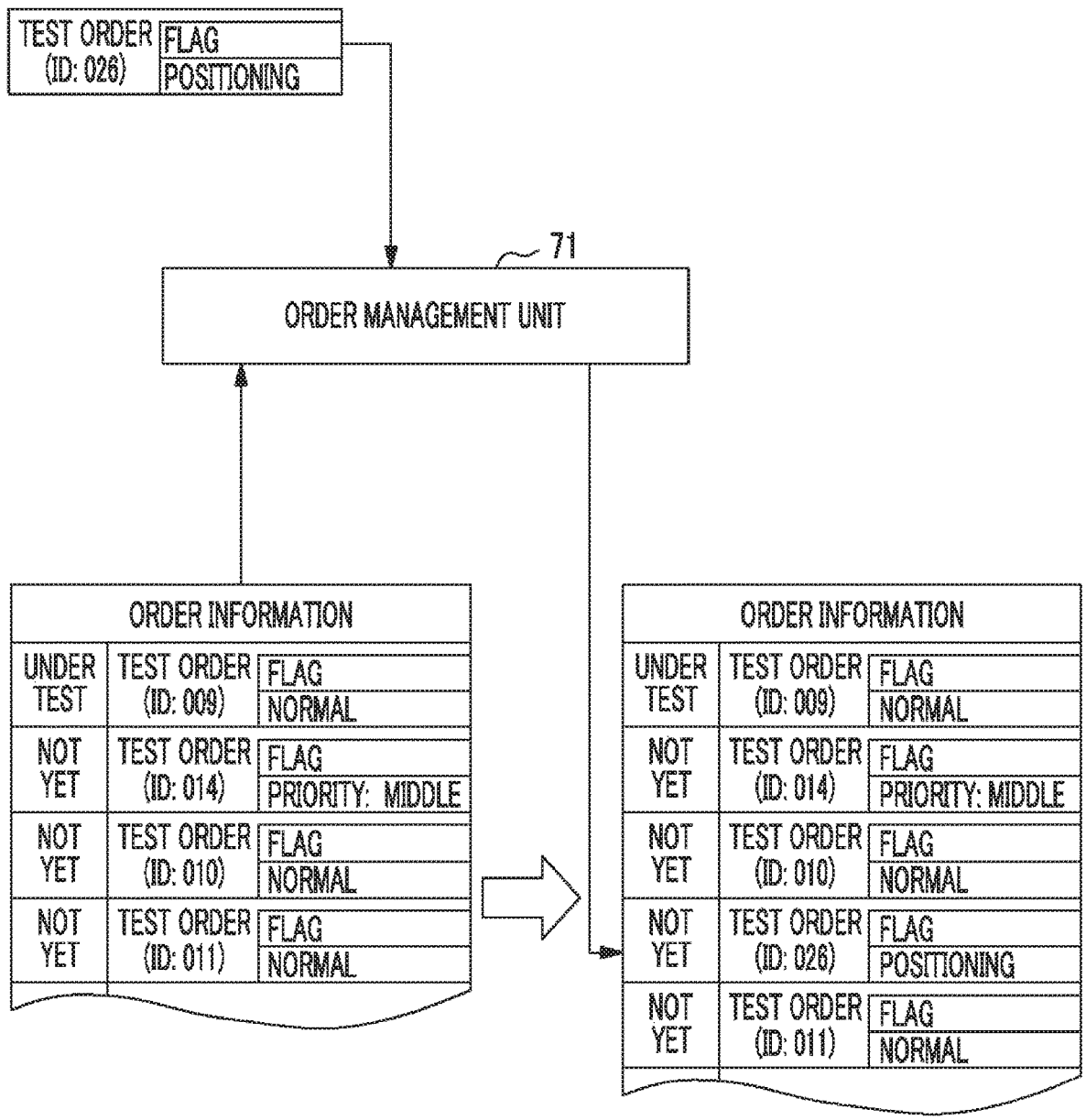
FIG. 22 is an explanatory view of a positioning interruption of Modification Example 2.

An example illustrated in FIG. 22 is an example of A positioning interruption in which a test order whose interrupt position is manually specified is interrupted. Also in FIG. 22, the order information before the execution of interrupt processing is the same as the example of FIG. 20. In a case where the order management unit 71 has received a new test order whose interrupt position is specified, the order management unit 71 registers the received test order at a specified position. For example, in a case where the interrupt position is specified between ID: 010 and ID: 011, as illustrated in FIG. 22, a new test order (ID: 026) is registered between ID: 010 and ID: 011.

Figure 23:
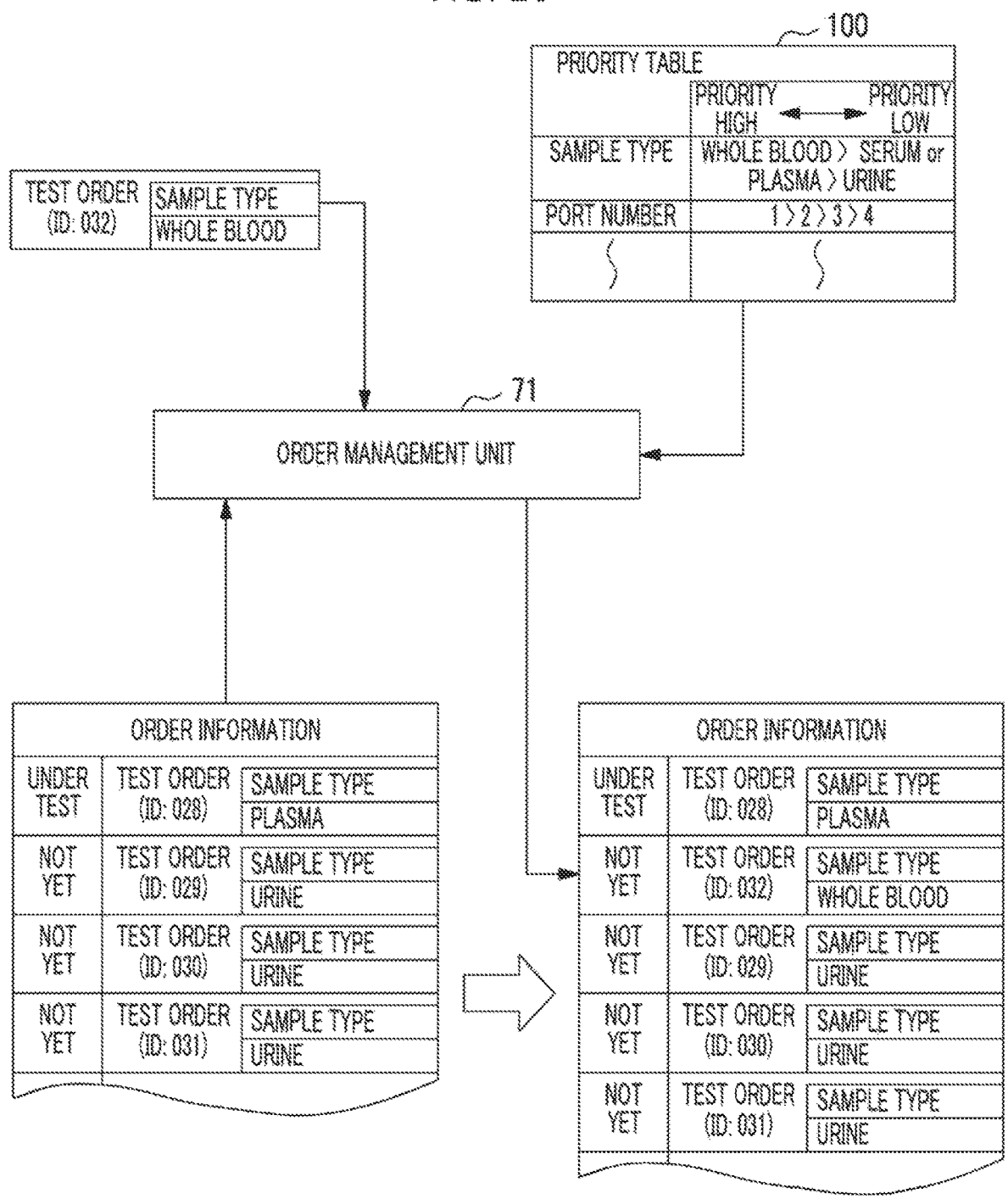
FIG. 23 is an explanatory view of a preferential interruption of Modification Example 2 that is different from FIG. 20.

An example illustrated in FIG. 23 is an example of a preferential interruption different from the preferential interruption illustrated in FIG. 20. In the example of FIG. 20, the interrupt processing of the test order is performed according to the priority specified by the test technician or the doctor of the requester, while in the example of FIG. 23, the interrupt processing of a test order is performed in accordance with a preset priority table 100.

For example, regarding sample types (whole blood, plasma or blood serum, urine, and the like) and the port numbers of the sample ports (refer to the sample plate 37 of FIG. 4), priorities are set in the priority table 100. In the sample types, the priorities are higher in order of "whole blood", "plasma or blood serum", and "urine", and the priorities are higher in order of "1", "2", "3", and "4" regarding the sample ports.

Sample type information is included in a test order. Additionally, after the sample set (the sample container 16 and the cartridge 18) is set in the sample plate 37, the port number of a sample port is set in the test order by the test technician.

The order management unit 71 performs the interrupt processing of a new test order with reference to the priority table 100 on the basis of a sample type and a port number that are included in a test order in a case where the test order is newly received.

In the example of FIG. 23, as the order information before the execution of interrupt processing, the sample type of a test order under measurement is "plasma", and all the sample types of test orders under standby are "urine". The order management unit 71 reads the sample type of a new test order (ID: 032). Then, since the sample type is "whole blood", the order management unit 71 investigates the priority of the "whole blood" with reference to the priority table 100. The priority of the "whole blood" is higher than the "urine" that are the sample types of the test orders under standby. For that reason, the order management unit 71 determines the interrupt position of the new test order (ID: 032) as the uppermost position (above ID: 029) among the positions of the test orders under standby, and registers the new test order (ID: 032) in the determined position.

In the present example, although the sample types have been described as examples, the same may be said of the port numbers. The order management unit 71 determines the interrupt position with reference to the priority table 100 on the basis of the port number of the new test order. Additionally, in a case where a plurality of kinds of information whose priorities are set like the sample types and the port numbers of the priority table 100 are is present, and in a case where both compete with each other, it is also preferable to set, in the priority table 100, information (for example, such as always prioritizing the sample types over the port numbers) on which one is prioritized.

Additionally, although the sample types and the port numbers are explained as examples of priority information, the priority information may be other than the same types and the port numbers. For example, the priorities may be set in accordance with measurement types (general chemical testing, enzyme testing, electrolyte testing, immunological testing, and the like). Additionally, the priorities may be set in accordance with user IDs of users who executes testing, such as a test technician, and IDs of patients to be tested. In a case where the priorities are set with the user IDs, for example, the usage of setting higher priorities for users who take charge of lifesaving and first-aiding is considered. Additionally, in a case where the priorities are set with the patient IDs, for example, the usage of setting higher priorities for patients with critical diseases is considered.

Figure 24:
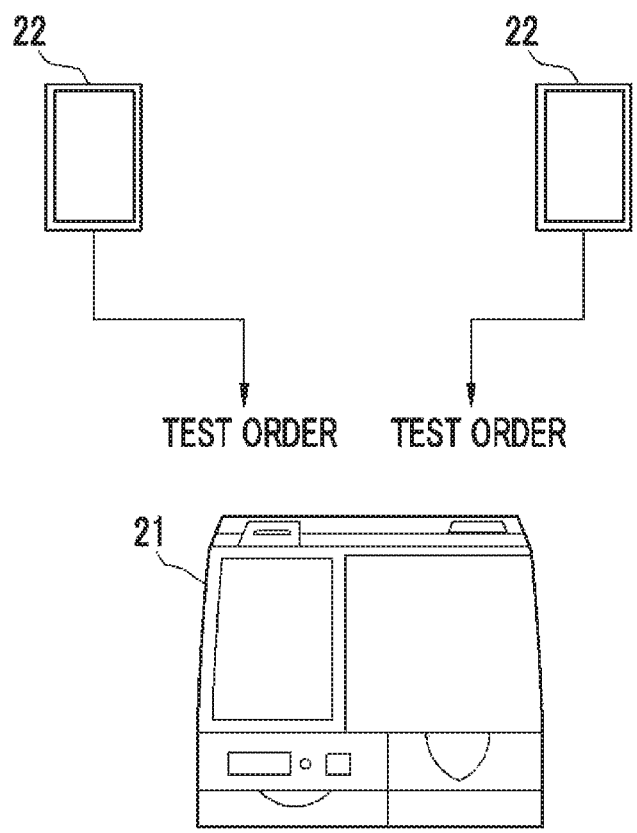
FIG. 24 is an explanatory view illustrating a usage example of Modification Example 2.

As illustrated in FIG. 24, it is also possible to input test orders from the mobile terminal 22 other than the diagnosis and treatment department terminal 13. Also, in the device main body 21, it is possible to register the plurality of mobile terminals 22 in the terminal management information. Thus, test orders may be transmitted from the plurality of mobile terminals 22 to the one device main body 21. In this way, in a case where a plurality of transmission sources for the test orders are present, the need for adjusting the turns of processing in accordance with the priorities of the plurality of test orders, or the like, increases. For that reason, the function of interrupting a test order by the order management unit 71 illustrated in FIGS. 20 to 23 is particularly useful for devices in which the test device 10 can perform reception of the test orders from the plurality of transmission sources, like the device main body 21.

Modification Example 3

Figure 25:
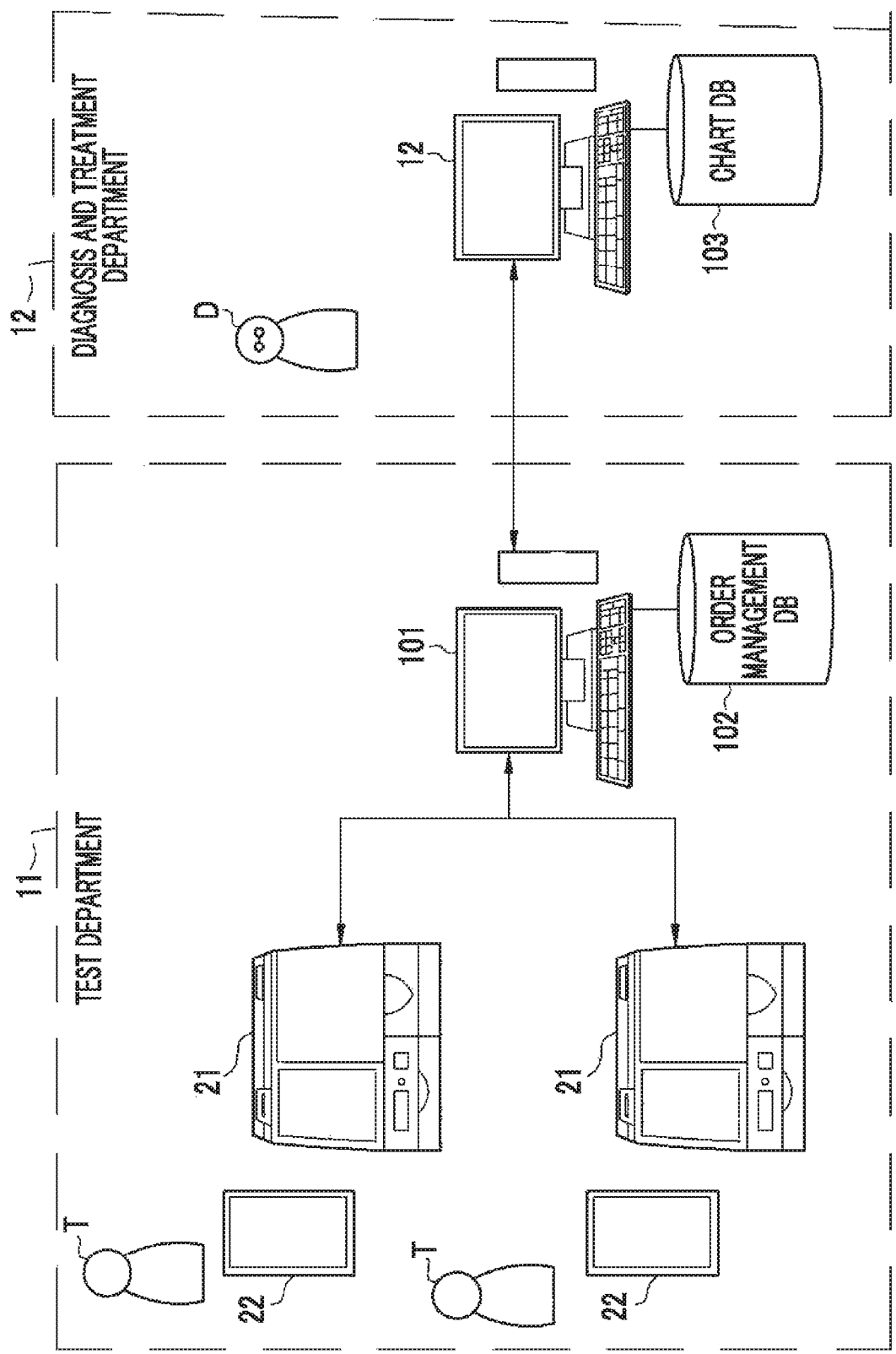
FIG. 25 is an explanatory view of a network system of Modification Example 3.
Figure 26:
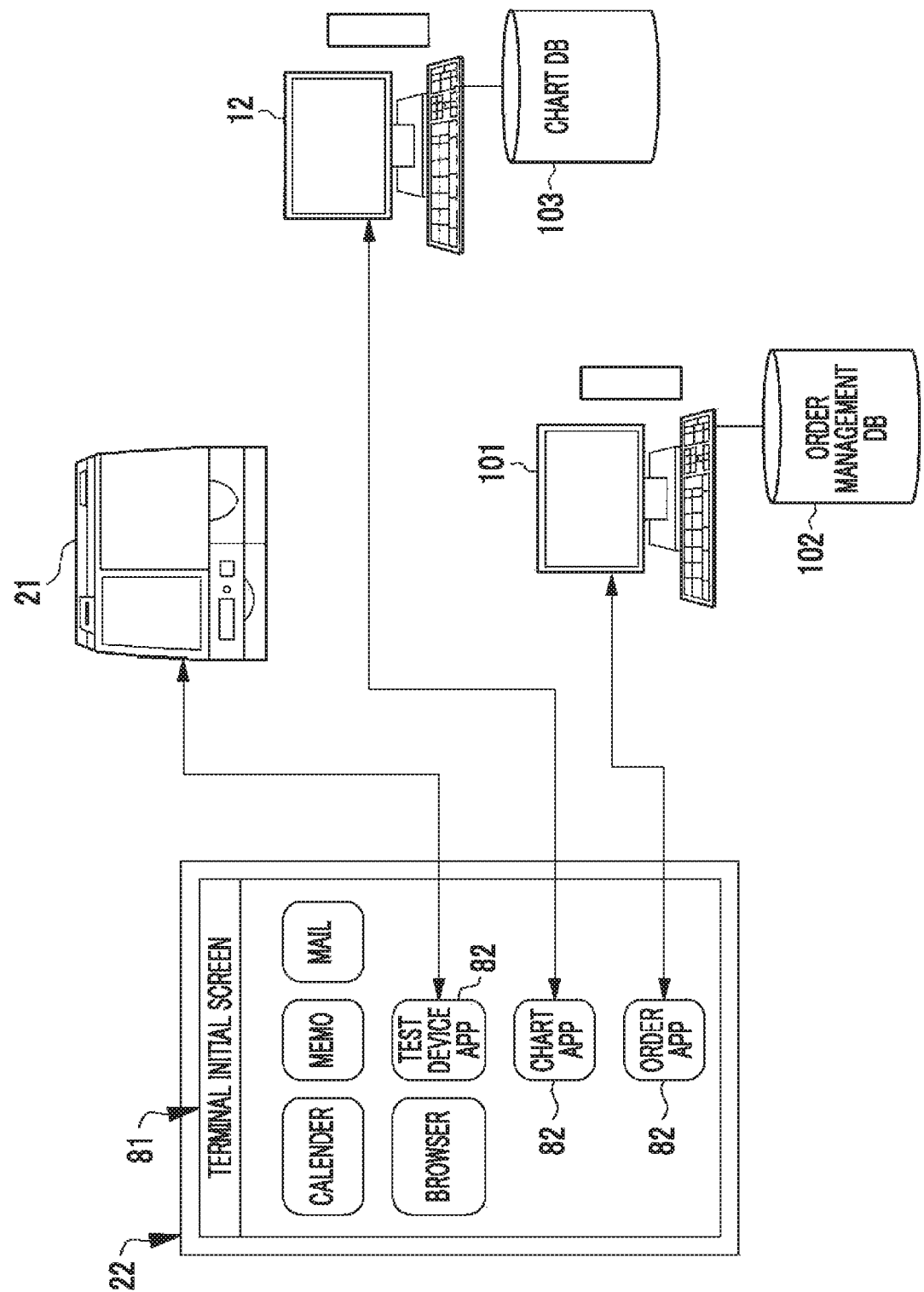
FIG. 26 is an explanatory view of a mobile terminal of Modification Example 3.

Modification Example 3 illustrated in FIGS. 25 and 26 is an example in which a plurality of test devices 10 and an order management server 101 are connected together to constitute a test system. The order management server 101 is a server that manages test orders. The order management server 101 receives test orders from client terminals by using the test device 10 and the diagnosis and treatment department terminal 13 as the client terminals, and registers the received test orders in a order management DB 102.

In a case where hospitals become large-scale, there are many cases where a plurality of test technicians T belong to the test department 11, and a plurality of test devices 10 are disposed arranged. Additionally, the number of diagnosis and treatment departments 12 also increases and the number of diagnosis and treatment department terminals 13 also increases. In such a case, since it is inconvenient to manage the test orders with one test device 10, it is preferable to make the order management server 101 carry the function of managing the test orders. The order management server 101, the device main bodies 21 of the plurality of test devices 10, the diagnosis and treatment department terminal 13, and the chart DB 103 are communicably connected to each other by the in-hospital LAN 14 to constitute a network system. The order management server 101 receives the test orders via the in-hospital LAN 14. Accordingly, a plurality of test orders having different input sources can be managed in a unified manner by the order management DB 102.

In a case where the network system is configured in this way, as illustrated in FIG. 26, the chart DB 103 and the order management DB 102 can be accessed from the mobile terminal 22 of the test device 10. In addition to the test device application, a chart application (chart app) and an order application (order app) are installed in the mobile terminal 22 as the client program. The icons 82 that starts the respective applications are displayed on the initial screen 81.

The chart application is a client program for making an access to the chart DB 103 to browse charts. The order application is a client program that makes an access to the order management DB 102 to browse test orders. Accordingly, the test technicians T can simply make an access to the order management DB 102 or the chart DB 103 from the mobile terminal 22. In addition, updating may be performed from the mobile terminal 22 in addition to the browsing of the charts and the test orders.

It is needless to say that the present invention is not limited to the above-described embodiments and the above-described modification examples and various configurations can be obtained unless departing from the scope of the present invention. For example, it is also possible to appropriately combine the above embodiments and the above above-described modification examples.

Moreover, since Modification Examples 1 to 3 respectively exhibit different effects independently from the first embodiment and the second embodiment, Modification Examples 1 to 3 are respectively carried out apart from the first embodiment and the second embodiment.

EXPLANATION OF REFERENCES

10: test device
21: device main body
22: mobile terminal
42: test unit
47: measuring part
48: wireless communication unit (transmission unit)
54: wireless communication unit (reception unit)
61: control unit
72: communication control unit
72A: determining unit
72B: notifying unit
94: transmission result display screen

What is claimed is:

1. A test device comprising:
a device main body having a test unit that tests a sample collected from a living body to output a plurality of pieces of measurement data and a transmission unit that wirelessly transmits the measurement data; and
a mobile terminal having a reception unit that receives the measurement data wirelessly transmitted from the transmission unit and a display unit that displays the received measurement data,
wherein the device main body further includes
a determining unit that determines whether or not the measurement data has been transmitted to the mobile terminal, and
a notifying unit that, in a case where there is non-transmitted data that has not transmitted among the plurality of pieces of measurement data, provides notification of a transmission result showing that there is the non-transmitted data to the mobile terminal,
wherein the determining unit receives, from the mobile terminal, notification of a reception result of the measurement data received by the mobile terminal after the measurement data is transmitted, and determines whether or not the measurement data has been transmitted on the basis of the reception result,
wherein the reception result includes received item information showing a measurement item of the measurement data received by the mobile terminal, and
wherein the determining unit determines whether or not transmission has been made by collating a measurement item of the transmitted measurement data with the received item information notified from the mobile terminal.

2. The test device according to claim 1,
wherein information on whether or not each piece of the measurement data has been transmitted is included in the transmission result.

3. The test device according to claim 2,
wherein the test unit tests a plurality of different samples and outputs a plurality of pieces of measurement data for each sample, and the measurement data to be transmitted by the transmission unit is the plurality of pieces of measurement data for each sample.

4. The test device according to claim 2,
wherein the test unit outputs a plurality of pieces of measurement data relating to a plurality of measurement items in testing of one sample, and
wherein the measurement data to be transmitted by the transmission unit is the plurality of pieces of measurement data regarding the plurality of measurement items.

5. The test device according to claim 3,
wherein the test unit outputs a plurality of pieces of measurement data relating to a plurality of measurement items in testing of one sample, and
wherein the measurement data to be transmitted by the transmission unit is the plurality of pieces of measurement data regarding the plurality of measurement items.

6. The test device according to claim 2,
wherein the determining unit receives, from the mobile terminal, notification of a reception result of the measurement data received by the mobile terminal after the measurement data is transmitted, and determines whether or not the measurement data has been transmitted on the basis of the reception result.

7. The test device according to claim 3,
wherein the determining unit receives, from the mobile terminal, notification of a reception result of the measurement data received by the mobile terminal after the measurement data is transmitted, and determines whether or not the measurement data has been transmitted on the basis of the reception result.

8. The test device according to claim 4,
wherein the determining unit receives, from the mobile terminal, notification of a reception result of the measurement data received by the mobile terminal after the measurement data is transmitted, and determines whether or not the measurement data has been transmitted on the basis of the reception result.

9. The test device according to claim 5,
wherein the determining unit receives, from the mobile terminal, notification of a reception result of the measurement data received by the mobile terminal after the measurement data is transmitted, and determines whether or not the measurement data has been transmitted on the basis of the reception result.

10. The test device according to claim 1,
wherein the reception result includes a received data size regarding the measurement data received by the mobile terminal, and
wherein the determining unit determines whether or not transmission has been made by collating a data size of the transmitted measurement data with the received data size notified from the mobile terminal.

11. The test device according to claim 1,
wherein the reception result includes received item information showing a measurement item of the measurement data received by the mobile terminal, and
wherein the determining unit determines whether or not transmission has been made by collating a measurement item of the transmitted measurement data with the received item information notified from the mobile terminal.

12. The test device according to claim 1,
wherein in a case where the non-transmitted data is generated due to a communication failure, the notifying unit notifies the mobile terminal of the transmission result in a case where the communication failure is recovered.

13. The test device according to claim 2,
wherein in a case where the non-transmitted data is generated due to a communication failure, the notifying unit notifies the mobile terminal of the transmission result in a case where the communication failure is recovered.

14. The test device according to claim 3,
wherein in a case where the non-transmitted data is generated due to a communication failure, the notifying unit notifies the mobile terminal of the transmission result in a case where the communication failure is recovered.

15. The test device according to claim 4,
wherein in a case where the non-transmitted data is generated due to a communication failure, the notifying unit notifies the mobile terminal of the transmission result in a case where the communication failure is recovered.

16. The test device according to claim 1,
wherein the notifying unit notifies a terminal different from the mobile terminal of the transmission result.

17. The test device according to claim 1,
wherein the mobile terminal functions as an operation terminal of the device main body.

18. A method of a device main body communicating with a mobile terminal, the device main body having a test unit that tests the sample collected from the living body, the method comprising:
wirelessly transmitting, to the mobile terminal, a plurality of pieces of measurement data outputted by the test unit;
receiving, from the mobile terminal, notification of a reception result of the measurement data received by the mobile terminal after the measurement data is transmitted;
determining whether or not the measurement data has been transmitted from the device main body to the mobile terminal on the basis of the reception result; and
providing, to the mobile terminal, notification of a transmission result showing that there is the non-transmitted data in a case where there is non-transmitted data that has not transmitted among the plurality of pieces of measurement data,
wherein the reception result of the measurement data includes received item information showing a measurement item of the measurement data received by the mobile terminal, and
wherein whether or not transmission has been made is determined by collating a measurement item of the transmitted measurement data with the received item information received from the mobile terminal.

* * * * *